(12) United States Patent
Johansson

(10) Patent No.: US 9,402,883 B2
(45) Date of Patent: *Aug. 2, 2016

(54) COMPOUND AND METHOD FOR TREATMENT OF ALZHEIMER'S DISEASE

(71) Applicant: ALPHABETA AB, Djursholm (SE)

(72) Inventor: Jan Johansson, Stockholm (SE)

(73) Assignee: ALPHARETA AB, Djursholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/279,589

(22) Filed: May 16, 2014

(65) Prior Publication Data

US 2014/0243272 A1 Aug. 28, 2014

Related U.S. Application Data

(63) Continuation of application No. 13/145,096, filed as application No. PCT/SE2010/050097 on Jan. 29, 2010, now Pat. No. 8,785,390.

(60) Provisional application No. 61/148,541, filed on Jan. 30, 2009.

(30) Foreign Application Priority Data

Jan. 30, 2009 (EP) ..................................... 09151790

(51) Int. Cl.
*A61K 38/00* (2006.01)
*A61K 38/28* (2006.01)
*A61K 38/17* (2006.01)
*C07K 14/785* (2006.01)

(52) U.S. Cl.
CPC ............. *A61K 38/395* (2013.01); *C07K 14/785* (2013.01); *A61K 38/00* (2013.01); *A61K 38/1709* (2013.01)

(58) Field of Classification Search
None
See application file for complete search history.

(56) References Cited

U.S. PATENT DOCUMENTS

| | | | |
|---|---|---|---|
| 8,211,442 B2 | 7/2012 | Kido et al. | |
| 8,268,321 B2 | 9/2012 | Kido et al. | |
| 8,785,390 B2* | 7/2014 | Johansson | 514/17.8 |
| 2002/0119463 A1 | 8/2002 | Faris et al. | |
| 2003/0224982 A1 | 12/2003 | Li et al. | |
| 2005/0070477 A1* | 3/2005 | Cochrane | 514/12 |
| 2007/0141073 A1 | 6/2007 | Kido et al. | |
| 2009/0130131 A1 | 5/2009 | Kido et al. | |
| 2012/0122794 A1 | 5/2012 | Johansson | |
| 2013/0172262 A1 | 7/2013 | Johansson | |
| 2014/0030274 A1 | 1/2014 | Johansson et al. | |

FOREIGN PATENT DOCUMENTS

| | | |
|---|---|---|
| WO | WO-88/03170 A1 | 5/1988 |
| WO | WO-00/71671 A2 | 11/2000 |
| WO | WO-02/41002 A2 | 5/2002 |
| WO | WO-03/090682 A2 | 11/2003 |
| WO | WO-2004/056310 A2 | 7/2004 |
| WO | WO-2005/023833 A2 | 3/2005 |
| WO | WO-2005/047484 A2 | 5/2005 |
| WO | WO-2005/055994 A1 | 6/2005 |
| WO | WO-2005/097182 A1 | 10/2005 |
| WO | WO-2006/138355 A2 | 12/2006 |
| WO | WO-2007/005672 A2 | 1/2007 |
| WO | WO-2007/018152 A1 | 2/2007 |
| WO | WO-2008/066734 A2 | 6/2008 |
| WO | WO-2008/151235 A2 | 12/2008 |
| WO | WO-2009/009396 A2 | 1/2009 |

OTHER PUBLICATIONS

Casals et al. "C-terminal, endoplasmic reticulum-lumenal domain of prosurfactant protein C—structural features and membrane interactions" FEBS Journal, 2008, vol. 275, No. 3.
Chaudhuri, T., et al. (2006), "Protein-misfolding diseases and chaperone-based therapeutic approaches", *The FEBS Journal*, 273: 1331-1349.
Citron, M. (2010), "Alzheimer's disease: strategies for disease modification", *Nature Reviews*, 9: 387-398.
DebBurman, S., et al. (1997), "Chaperone-supervised conversion of prion protein to its protease-resistant form" *Proc. Natl. Acad Sci. USA*, 94:13938-13943.
Evans, C., et al. (2006), "Heat shock proteins 70 and 90 inhibit early stages of amyloid β-(1-42) aggregation in vitro" *The Journal of Biological Chemistry*, 281(44):33182-33191.
Extended European Search Report dated Jul. 17, 2009 issued in EP Application No. 09151790.4.
Fitzen, Michael et al. "Peptide-binding specificity of the prosurfactant protein C Brichos domain analyzed by electrospray ionization mass spectrometry", Rapid Commun. Mass Spectrom. 2009; 23: 3591-3598.
Fotinopoulou, A., et al. (2005) "BRI2 Interacts with amyloid precursor protein (APP) and regulates amyloid β (Aβ) production" *The Journal of Biological Chemistry*, 280(35): 30768-30772.
Hellstrand, E., et al. (2010) "Amyloid β-protein aggregation produces highly reproducible kinetic data and occurs by a two-phase process" *ACS Chemical Neuroscience*, 1:13-18.
International Preliminary Report on Patentability dated Sep. 15, 2010 issued in PCT Application No. PCT/SE2010/050097.
International Preliminary Report on Patentability dated Dec. 28, 2012 issued in PCT Application No. PCT/SE2010/050723.
International Preliminary Report on Patentability dated Oct. 8, 2013 issued in PCT Application No. PCT/SE2012/050352.
International Search Report and Written Opinion dated Mar. 18, 2010 issued in PCT Application No. PCT/SE2010/050097.

(Continued)

*Primary Examiner* — Olga N Chernyshev
(74) *Attorney, Agent, or Firm* — Harness, Dickey and Pierce, P.L.C.

(57) ABSTRACT

An isolated protein selected from the group consisting of (i) proteins comprising an amino acid sequence having at least 70% identity to the C-terminal domain of lung surfactant protein C precursor (CTproSP-C, "CTC") from a mammal; and (ii) proteins comprising an amino acid sequence having at least 70% identity to the Brichos domain of CTproSP-C from a mammal, is disclosed for treatment of Alzheimer's disease in a mammal, including man.

6 Claims, 11 Drawing Sheets

(56) References Cited

OTHER PUBLICATIONS

International Search Report and Written Opinion dated Feb. 3, 2011 issued in PCT Application No. PCT/SE2010/050723.

International Search Report dated Sep. 11, 2012 issued in PCT Application No. PCT/SE2012/050352.

Johansson, H., et al. (2009), "Preventing amyloid formation by catching unfolded transmembrane segments", *J. Mol. Biol.*, 389: 227-229.

Johansson, J. (2003), "Molecular determinants for amyloid fibril formation: lessons from lung surfactant protein C", *Swiss Med Wkly*, 133: 275-282.

Johansson, J., et al. (2006), "The brichos domain-containing C-terminal part of pro-surfactant protein C binds to an unfolded poly-val-transmembrane segment", *The Journal of Biological Chemistry*, 281(30): 21032-21039.

Kim, J., et al. (2008), "BRI2 (ITM2b) inhibits Aβ deposition In Vivo", The Journal of neuroscience, 28(23): 6030-6036.

Klucken, J., et al. (2004), "Hsp70 reduces α-synuclein aggregation and toxicity", *The Journal of Biological Chemistry*, 279(4): 25497-25502.

Martin, L., et al. (2008), "Regulated intramembrane proteolysis of Bri2 (Itm2b) by ADAM10 and SPPL2a/SPPL2b" *The Journal of Biological Chemistry*, 283(3):1644-1652.

Matsubara, E., et al. (1996), "Apolipoprotein J and alzheimer's amyloid β solubility" *Biochem J.*, 316:671-679.

Matsuda, S., et al. (2009), "Maturation of BRI2 generates a specific inhibitor that reduces APP processing at the plasma membrane and in endocytic vesicles" *Neurobiology of Aging*, 7384:1-9.

McHattie, S., et al. (1999), "Clusterin prevents aggregation of neuropeptide 106-126 in vitro" *Biochemical and Biophysical Research Communications*, 259:336-340.

Nerelius, C., et al. (2008), "Mutations Linked to interstitial lung disease can abrogate anti-amyloid function of prosurfactant protein C", *Biochem J.*, 416: 201-209.

Nerelius, C., et al. (2009), "Anti-amyloid activity of the C-terminal domain of proSP-C against amyloid β-peptide and medin", *Biochemistry*, 48: 3778-3786.

Nerelius, C., et al. (2010), "Amino Acid sequence determinants and molecular chaperones in amyloid fibril formation", *Biochemical and Biophysical Research Communications*, 396: 2-6.

Office Action dated Oct. 10, 2013 issued in U.S. Appl. No. 13/805,574.

Office Action dated Oct. 15, 2012 issued in U.S. Appl. No. 13/145,096.

Office Action dated Jan. 16, 2014 issued in U.S. Appl. No. 14/009,360.

Office Action dated Feb. 27, 2013 issued in U.S. Appl. No. 13/145,096.

Office Action dated Aug. 29, 2013 issued in U.S. Appl. No. 13/145,096.

Office Action dated Jul. 31, 2013 issued in U.S. Appl. No. 13/805,574.

Peng, S., et al. (2010), "The extracellular domain of Bri2 (ITM2B) binds the ABri peptide (1-23) and amyloid β-peptide (Aβ1-40): Implications for Bri2 effects on processing of amyloid precursor protein and Aβ aggregation" *Biochemical and Biophysical Research Communications*, 393:356-361.

Shimshek, D., et al. (2010), "The HSP70 molecular chaperone is not beneficial in a mouse model of α-synucleinopathy", *PLoS ONE*, 5(4): e10014.

Sánchez-Pulido, L., et al. (2002), "BRICHOS: a conserved domain in proteins associated with dementia, respiratory distress and cancer" *Trends in Biochemical Sciences*, 27(7):329-332.

Thompson, J., et al. (1994), "Clustal W: improving the sensitivity of progressive multiple sequence alignment through sequence weighting, position-specific gap penalties and weight matrix choice", *Oxford University Press*, 22(22): 4673-4680.

Tomidokoro, Y., et al. (2005) "Familial Danish dementia co-existence of Danish and Alzheimer amyloid subunits (ADan and Aβ) in the absence of compact plaques" *The Journal of Biological Chemistry*, 280(44):36883-36894.

Vickers, J., (2002), "A vaccine against alzheimer's disease", *Drugs Aging*, 19(7):487-494.

Westermark, P., (2005), "Aspects on human amyloid forms and their fibril polypeptides", *The FEBS Journal*, 5942-5949.

Bowie, J.U., et al. (1990) "Deciphering the message in protein sequences: tolerance to amino acid substitutions", *Science*, 247(4948):1306-1310.

Burgess, W.H., et al. (1990) "Possible dissociation of the heparian-binding and mitogenic activities of heparin-binding (acidic fibroblast) growth factor-1 from its receptor-binding activities by site-directed mutagenesis of a singly lysine residue", *The Journal of Cell Biology*, 111:2129-2138.

Office Action dated Jul. 3, 2014 issued in U.S. Appl. No. 14/009,360.

Pawson, T., et al. (2003) "Assembly of cell regulatory systems through protein interaction domains", *Science*, 300:445-452.

Office Action dated Mar. 16, 2015 issued in U.S. Appl. No. 14/009,360.

Office Action dated Feb. 24, 2015 issued in U.S. Appl. No. 14/287,742.

Office Action dated Oct. 31, 2014 issued in U.S. Appl. No. 14/287,742.

Database Accession No. O89051, created Nov. 1, 1998, "Integral membrane protein 2B".

Database Accession No. Q3T0P7, created Oct. 11, 2005, "Integral membrane protein 2B".

Database Accession No. Q52N47, created May 24, 2005, "Integral membrane protein 2B".

Database Accession No. Q5XIE8, created Nov. 23, 2004, "Integral membrane protein 2B".

\* cited by examiner

```
A                           proSP-C
        H2N_[            |    |            ]_COOH
                              ⇩
                       CTproSP-C
              H2N_[         ]_COOH       H2N_[            ]_COOH B
Bovine   HMSQKHTEMVLEMSIT-GPEAQQRLALSERVGTTATFSIGSTGTVVYDYQRLLIAYKPAPGTCCYIMKMAP
Human    HMSQKHTEMVLEMSIG-APEAQQRLALSEHLVTTATFSIGSTGLVVYDYQQLLIAYKPAPGTCCYIMKIAP
Rhesus   HMSQKHTEMVLEMSIG-APEAQQHLARSGHLVTTATFSFGSTGLVVYDYQRLLIAYKPAPGTWCYIMKTAP
Mouse    HMSQKHTEMVLEMSIG-APETQKRLAPSERADTIATFSIGSTGIVVYDYQRLLTAYKPAPGTYCYIMKMAP
Mink     HMSQKHTEMVLEMSLG-GPEAQQRLALQERAGTTATFSIGSTGIVVYDYQRLLIAYKPAPGTCCYIMKMAP
Rabbit   HMSQKHTEMVLEMSIG-APEVQQRLALSEWAGTTATFPIGSTGIVTCDYQRLLIAYKPAPGTCCYLMKMAP
Rat      HMSQKHTEMVLEMSIGGAPETQKRLALSEHTDTIATFSIGSTGIVLYDYQRLLTAYKPAPGTYCYIMKMAP
Strict   HMSQKHTEMVLEMS----PE-Q---LA------T-ATF--GSTG-V---DYQ-LL-AYKPAPGT-CY-MK-AP Bovine   QNIPSLEALTRKLQNFQ------AKPQVPSSKLGQEQGHDAGSAF--SG-DLAFLGRTVSTLCGEVPLYYT
Human    ESIPSLEALNRKVHNFQMECSLQAKPAVPTSKLGQAEGRDAGSAP--SGGDPAFLGMAVNTLCGEVPLYYI
Rhesus   ESIPSLEALTRKVQNFQ------AKPAVPTSKLDQVEGRDAGSAP--SRGDLAFLGMAVSTLCGEVPLYYI
Mouse    ESIPSLEAFARKLQNFR------AKPSTPTSKLGQEEGHDTGSESDSSGRDLAFLGLAVSTLCGELPLYYI
Mink     ENIPSLEALTRKFQNFQ------VKPAVSTSKLGQEEGHNAGSA---SPGDLDFLGTTVSTLCGEVPLYYI
Rabbit   DSIPSLEALARKFQANP------AEPPTQR---GQDKGPAAGPA--SSGGELAFLGAAVSTLCGEVPLIYI
Rat      ESIPSLEALARKFKNFQ------AKSSTPTSKLGQEEGHSAGSDSDSSGRDLAFLGLAVSTLCGELPLYYI
Strict   --IPSLEA--RK----------------------Q---G----G---S------FLG---V-TLCGE-PL-Y-

Fig. 1
```

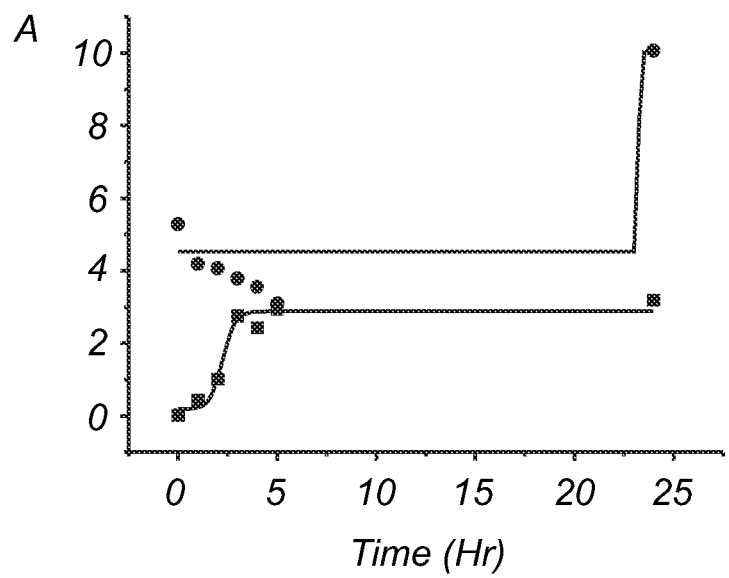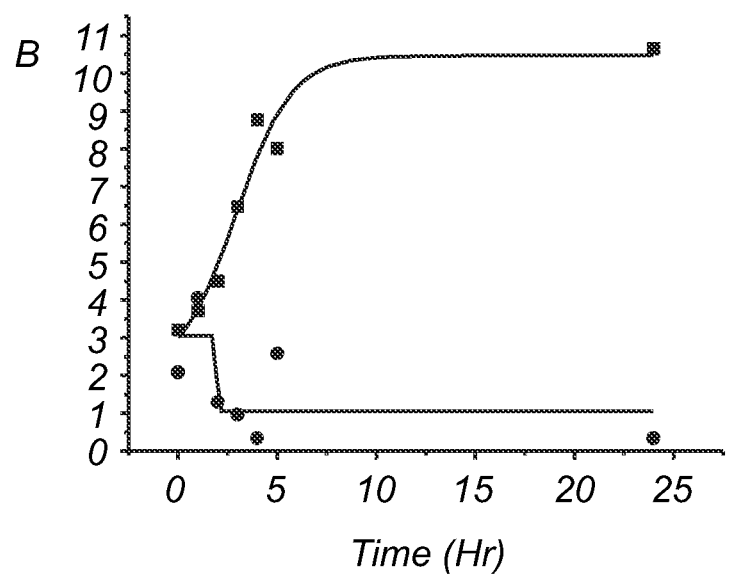
Fig. 12

COMPOUND AND METHOD FOR TREATMENT OF ALZHEIMER'S DISEASE

CROSS REFERENCE TO RELATED APPLICATIONS

This application is a Continuation of U.S. Ser. No. 13/145,096 filed on 6 Oct. 2011, which is a National Stage entry of International Application No. PCT/SE2010/050097, filed on 29 Jan. 2010, and which claims priority under 35 U.S.C. §119 to U.S. Provisional Application No. 61/148,541, filed on 30 Jan. 2009, and to EP Application No. 09151790.4, filed on 30 Jan. 2009. Each of the patent applications cited in this paragraph are hereby incorporated by reference in their entirety.

REFERENCE TO A SEQUENCE LISTING

The material in the ASCII text file entitled "61258173_1.txt" is hereby incorporated by reference in its entirety. The ASCII text file entitled "61258173_1.txt" was created on 21 May 2013 and the size is 31 KB.

FIELD OF THE INVENTION

The present invention pertains to the field of medicine. More specifically, this invention relates to medicaments for treatment and medical treatment of Alzheimer's disease in mammals, such as man.

BACKGROUND TO THE INVENTION

Alzheimer's disease is one of the most common causes of dementia in man. It is a chronic and fatal disease associated with neural cell degeneration in the brain of the affected individual, characterized by the presence of amyloid plaques consisting of extracellular deposits of amyloid β-peptide (Aβ-peptide). The neural cell atrophy caused by Aβ aggregation results in deficiency of acetylcholine and other signaling substances. It is known that Aβ-peptide, having 40-42 amino acid residues, is produced by processing of the amyloid precursor protein (APP), which is a membrane protein normally expressed by the neurons of the central nervous system, but the reasons for this processing are incompletely understood. The released Aβ peptide contains a part of the transmembrane region of APP (Aβ residues 29-40/42) and includes a discordant helix, i.e. a helix composed of amino acids with a high propensity to form β-strands. Aβ is prone to misfold and aggregate when removed from its stabilising membrane environment.

Current therapeutic approaches for treatment of Alzheimer's disease are mainly directed to treating the symptoms and include cholinergic replacement therapy, e.g. inhibition of acetylcholinesterase, small inhibitors that interact with soluble Aβ oligomers, and so-called β-sheet breakers that prevent elongation of already formed β-sheet structures.

Another suggested strategy to prevent aggregation has been to utilize molecules that are functionally defined as chaperones. Chaperones play an important role by aiding the correct folding of proteins in the complex intracellular milieu. A number of molecular chaperones, such as heat-shock proteins (Hsp), are known to be important in the folding process and have been extensively studied. Some of these chaperones are apparently able to interact with and have an impact on the amyloid fibril formation of certain polypeptides. Aggregation of $A\beta_{1-42}$ is inhibited by Hsp90 or the combination Hsp70/Hsp40 (C G Evans et al, J Biol Chem 281: 33182-33191, 2006). Furthermore, the extracellular chaperone clusterin (apolipoprotein J) has been shown to inhibit fibril formation of a number of polypeptides including Aβ (E Matsubara et al, Biochem J 316 (Pt 2): 671-679, 1996) and a fragment of the prion protein (S McHattie and N Edington, Biochem Biophys Res Commun 259: 336-340, 1999). The role of the structurally diverse chaperones in prevention of amyloid diseases is not established and some reports even indicate that protein chaperones promote amyloid fibril formation, see e.g. S K DebBurman et al. Proc Nat Acad Sci USA 94: 13938-13943, 1997. In addition to molecular chaperones, the effects of chemical and pharmacological chaperones have been studied in the context of misfolding diseases. No effective therapy using chaperones or other means has so far been found for any amyloid disease.

Monoclonal antibodies against Aβ peptide prevent aggregation into neurotoxic fibrils and dissolve already formed amyloid. However, antibody therapy is very costly and associated with side-effects of varying seriousness. Vaccination with β-amyloid in transgenic mice models of Alzheimer's disease has shown a significant reduction in the number of amyloid plaques and overall amyloid burden and even some improvement in cognitive performance.

SUMMARY OF THE INVENTION

It is an object of the invention to decrease aggregation of Aβ-peptide into amyloid fibrils.

It is also an object of the invention to decrease formation of amyloid plaques consisting of extracellular deposits of Aβ-peptide in the brain of a mammal.

It is another object of the invention to provide a new treatment option for the treatment of Alzheimer's disease in a mammal, including man.

For these and other objects that will be evident from the following description, the present invention provides an isolated protein selected from the group consisting of (i) proteins comprising an amino acid sequence having at least 70% identity to the C-terminal domain of lung surfactant protein C precursor (CTproSP-C) from human (SEQ ID NO: 2), bovine (SEQ ID NO: 5), rhesus (SEQ ID NO: 6), mouse (SEQ ID NO: 7), mink (SEQ ID NO: 8), rabbit (SEQ ID NO: 9) or rat (SEQ ID NO: 10); and (ii) proteins comprising an amino acid sequence having at least 70% identity to the Brichos domain of CTproSP-C from human (SEQ ID NO: 4), bovine (SEQ ID NO: 12), rhesus (SEQ ID NO: 13), mouse (SEQ ID NO: 14), mink (SEQ ID NO: 15), rabbit (SEQ ID NO: 16) or rat (SEQ ID NO: 17), for use as a medicament.

It has surprisingly been found that this isolated protein has the capacity to decrease amyloid fibril formation and reduce aggregation of Aβ-peptide. This is particularly surprising in view of the structural dissimilarity between the endogenous targets (SP-C and proSP-C) for the CTproSP-C chaperone activity and the Aβ-peptide that is associated with Alzheimer's disease. It is also highly surprising since the proSP-C gene is only expressed in lung tissue. The present invention is based on the herein disclosed, surprising insights about the substrate specificity of CTproSP-C, which was previously not known.

In one embodiment, the isolated protein is selected from the group consisting of proteins comprising an amino acid sequence having (a) all conserved residues of the Brichos domain of mammalian CTproSP-C (SEQ ID NO: 18), and (b1) at least 70% identity to CTproSP-C from human (SEQ ID NO: 2), bovine (SEQ ID NO: 5), rhesus (SEQ ID NO: 6), mouse (SEQ ID NO: 7), mink (SEQ ID NO: 8), rabbit (SEQ ID NO: 9) or rat (SEQ ID NO: 10); or (b2) at least 70% identity to the Brichos domain of CTproSP-C from human (SEQ ID NO: 4), bovine (SEQ ID NO: 12), rhesus (SEQ ID NO: 13), mouse (SEQ ID NO: 14), mink (SEQ ID NO: 15), rabbit (SEQ ID NO: 16) or rat (SEQ ID NO: 17). Put another way, this embodiment implies that in the corresponding positions, the isolated protein having all conserved residues of the Brichos domain of mammalian CTproSP-C (SEQ ID NO: 18) contains all the following conserved residues of the Brichos domain of human CTproSP-C (SEQ ID NO: 4): Phe-1, Gly-4, Ser-5, Thr-6, Gly-7, Val-9, Asp-12, Tyr-13, Gln-14, Leu-16, Leu-17, Ala-19, Tyr-20, Lys-21, Pro-22, Ala-23, Pro-24, Gly-25, Thr-26, Cys-28, Tyr-29, Met-31, Lys-32, Ala-34, Pro-35, Ile-38, Pro-39, Ser-40, Leu-41, Glu-42, Ala-43, Arg-46, Lys-47, Gln-70, Gly-73, Gly-77, Ser-81, Phe-87, Leu-88, Gly-89, Val-92, Thr-94, Leu-95, Cys-96, Gly-97, Glu-98, Pro-100, Leu-101 and Tyr-103.

In one embodiment, the isolated protein is selected from the group consisting of proteins comprising an amino acid sequence having (a) all conserved residues of mammalian CTproSP-C (SEQ ID NO: 11), and (b) at least 70% identity to CTproSP-C from human (SEQ ID NO: 2), bovine (SEQ ID NO: 5), rhesus (SEQ ID NO: 6), mouse (SEQ ID NO: 7), mink (SEQ ID NO: 8), rabbit (SEQ ID NO: 9) or rat (SEQ ID NO: 10). Put another way, this embodiment implies that in the corresponding positions, the isolated protein having all conserved residues of mammalian CTproSP-C (SEQ ID NO: 11) contains all the following conserved residues of human CTproSP-C (SEQ ID NO: 2): His-1, Met-2, Ser-3, Gln-4, Lys-5, His-6, Thr-7, Glu-8, Met-9, Val-10, Leu-11, Glu-12, Met-13, Ser-14, Pro-18, Glu-19, Gln-21, Leu-24, Ala-25, Thr-32, Ala-34, Thr-35, Phe-36, Gly-39, Ser-40, Thr-41, Gly-42, Val-44, Asp-47, Tyr-48, Gln-49, Leu-51, Leu-52, Ala-54, Tyr-55, Lys-56, Pro-57, Ala-58, Pro-59, Gly-60, Thr-61, Cys-63, Tyr-64, Met-66, Lys-67, Ala-69, Pro-70, Ile-73, Pro-74, Ser-75, Leu-76, Glu-77, Ala-78, Arg-81, Lys-82, Gln-105, Gly-108, Gly-112, Ser-116, Phe-122, Leu-123, Gly-124, Val-127, Thr-129, Leu-130, Cys-131, Gly-132, Glu-133, Pro-135, Leu-136 and Tyr-138. In an embodiment, the isolated protein is selected from the group consisting of (i) proteins comprising an amino acid sequence having at least 70% identity to human CTproSP-C (SEQ ID NO: 2), and (ii) proteins comprising an amino acid sequence having at least 70% identity to the Brichos domain of human CTproSP-C (SEQ ID NO: 4). In certain embodiments, the isolated protein according to the present invention consists of less than or equal to 500, such as less than or equal to 250, such as less than or equal to 200, such as less than or equal to 150 amino acid residues. In certain embodiments, the isolated protein according to the present invention consists of more than or equal to 90, such as more than or equal to 100, such as more than or equal to 150 amino acid residues. A preferable size range is 90-200 amino acid residues, such as 100-150 amino acid residues. In one embodiment, the isolated protein is selected from the group consisting of (i) CTproSP-C from human (SEQ ID NO: 2), bovine (SEQ ID NO: 5), rhesus (SEQ ID NO: 6), mouse (SEQ ID NO: 7), mink (SEQ ID NO: 8), rabbit (SEQ ID NO: 9) or rat (SEQ ID NO: 10), and (ii) Brichos domains of CTproSP-C from human (SEQ ID NO: 4), bovine (SEQ ID NO: 12), rhesus (SEQ ID NO: 13), mouse (SEQ ID NO: 14), mink (SEQ ID NO: 15), rabbit (SEQ ID NO: 16) or rat (SEQ ID NO: 17).

In specific embodiments, the isolated protein is selected from the group consisting of human CTproSP-C (SEQ ID NO: 2), the Brichos domain of human CTproSP-C (SEQ ID NO: 4), and an extended Brichos domain of CTproSP-C from human having SEQ ID NO: 21. An advantage of the extended Brichos domain having SEQ ID NO: 21 is that is more stable than the Brichos domain, while both the Brichos domain and the extended Brichos domain have the same function as the full-length CTproSP-C protein. In a certain embodiment, the isolated protein is human CTproSP-C (SEQ ID NO: 2). In another certain embodiment, the isolated protein is the Brichos domain of human CTproSP-C (SEQ ID NO: 4).

In one embodiment, the position corresponding to leucine-188 in human proSP-C (SEQ ID NO: 1) is not glutamine. In a further embodiment, the position corresponding to leucine-188 in human proSP-C (SEQ ID NO: 1) is strictly conserved.

According to an embodiment, the isolated protein is suitable for use in treatment of Alzheimer's disease, including dementia of the Alzheimer type, in a mammal, including man.

According to one embodiment, the present invention provides a treatment that is selected from the group consisting of preventive, palliative and curative treatment.

According to another aspect, the present invention provides a pharmaceutical composition comprising a therapeutically effective amount of the isolated protein according to the invention and a suitable pharmaceutical carrier therefor.

According to one embodiment, the pharmaceutical composition is useful in treatment of Alzheimer's disease in a mammal, including man. According to one aspect, the present invention provides a method of treating Alzheimer's disease in a mammal, including man, in need thereof comprising administration to said mammal of a therapeutically effective amount of the isolated protein according to the invention or the pharmaceutical composition according to the invention.

According to one embodiment, the present invention provides a treatment that is selected from the group consisting of preventive, palliative and curative treatment.

According to another aspect, the present invention provides use of an isolated protein according to the invention for the manufacture of a medicament for the treatment of Alzheimer's disease in a mammal, including man.

BRIEF DESCRIPTION OF THE DRAWINGS

FIG. 1 A shows a schematic outline of proSP-C processing and 1 B shows an alignment of known mammalian CTproSP-C amino acid sequences: Bovine (SEQ ID NO:5); Human (SEQ ID NO:2); Rhesus (SEQ ID NO:6); Mouse (SEQ ID NO:7); Mink (SEQ ID NO:8); Rabbit (SEQ ID NO:9); Rat (SEQ ID NO:10); Strictly conserved residues (SEQ ID NO:11).

FIG. 2 B shows the sequence of SP-$C^{I23V}$ (SEQ ID NO:38).

FIG. 12 panels A and B show the amplitude of the CD signal at 217 nm over time for Aβ(1-40) as well as Aβ(1-42) with and without CTproSP-C.

LIST OF APPENDED SEQUENCES

Figure 2:
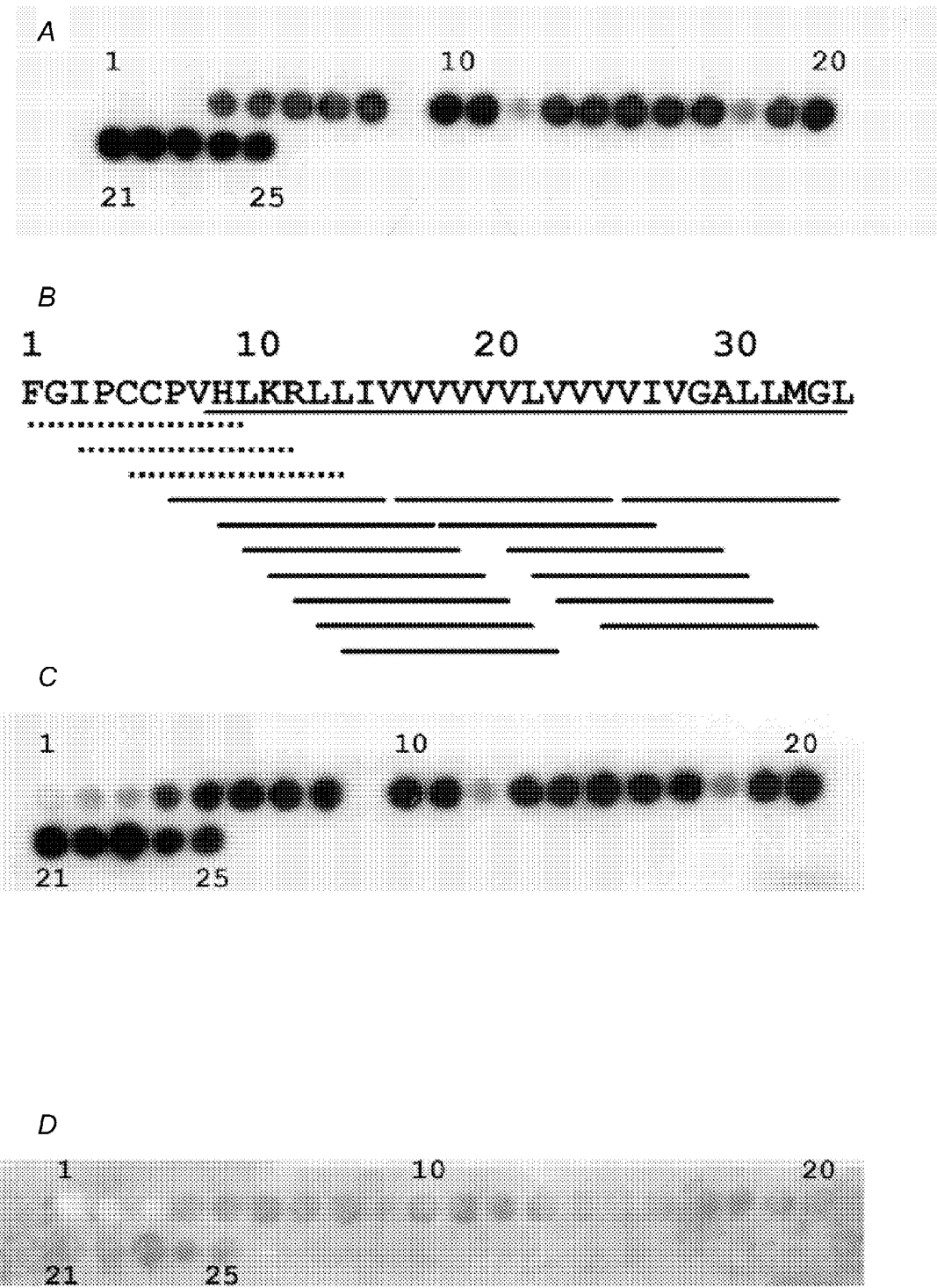
FIG. 2 panels A, C, and D show binding of CTproSP-$C_{Brichos}$ and CTproSP-C to SP-C derived peptide spots on cellulose membranes.

SEQ ID NO: 1 human proSP-C
SEQ ID NO: 2 human CTproSP-C
SEQ ID NO: 3 human SP-C
SEQ ID NO: 4 human CTproSP-C$_{Brichos}$
SEQ ID NO: 5 bovine CTproSP-C
SEQ ID NO: 6 rhesus macaque CTproSP-C
SEQ ID NO: 7 mouse CTproSP-C
SEQ ID NO: 8 mink CTproSP-C
SEQ ID NO: 9 rabbit CTproSP-C
SEQ ID NO: 10 rat CTproSP-C
SEQ ID NO: 11 conserved mammalian CTproSP-C
SEQ ID NO: 12 bovine CTproSP-C$_{Brichos}$
SEQ ID NO: 13 rhesus macaque CTproSP-C$_{Brichos}$
SEQ ID NO: 14 mouse CTproSP-C$_{Brichos}$
SEQ ID NO: 15 mink CTproSP-C$_{Brichos}$
SEQ ID NO: 16 rabbit CTproSP-C$_{Brichos}$
SEQ ID NO: 17 rat CTproSP-C$_{Brichos}$
SEQ ID NO: 18 conserved mammalian CTproSP-C$_{Brichos}$
SEQ ID NO: 19 human Aβ peptide$_{1-40}$
SEQ ID NO: 20 S-tagged human CTproSP-C
SEQ ID NO: 21 human CTproSP-C$_{Brichos\ 86-197}$
SEQ ID NO: 22 LVFF peptide
SEQ ID NO: 23 IIGLMVGGW peptide
SEQ ID NO: 24 CTproSP-C(Brichos) forward amplification primer
SEQ ID NO: 25 CTproSP-C(Brichos) reverse amplification primer
SEQ ID NO: 26 peptide corresponding to positions 11-20 in human SP-C
SEQ ID NO: 27 mutant of human SP-C residues 11-20, where isoleucines
  and valines are all replaced with leucines
SEQ ID NO: 28 mutant of human SP-C residues 11-20, where leucines,
  isoleucines and valines are all replaced with alanines
SEQ ID NO: 29 peptide corresponding to positions 12-21 in human SP-C
SEQ ID NO: 30 mutant of human SP-C residues 12-21, where isoleucines
  and valines are all replaced with leucines
SEQ ID NO: 31 mutant of human SP-C residues 12-21, where leucines,
  isoleucines and valines are all replaced with alanines
SEQ ID NO: 32 peptide corresponding to positions 17-26 in SP-C$^{I23V}$
SEQ ID NO: 33 poly-leucine 10-mer peptide
SEQ ID NO: 34 poly-alanine 10-mer peptide
SEQ ID NO: 35 peptide corresponding to positions 22-31 in SP-C$^{I23V}$
SEQ ID NO: 36 ambivalently helical hydrophobic 18-mer peptide
SEQ ID NO: 37 control, non-target 6-mer peptide
SEQ ID NO: 38 Mutant version of human SP-C sequence with valine
  substituted for isoleucine at position 23 (SP-C$^{I23V}$).

DETAILED DESCRIPTION OF THE INVENTION

It has surprisingly been found that CTproSP-C (also known as "CTC"), proteins comprising an amino acid sequence having at least 70% identity to a mammalian CTproSP-C, and proteins comprising an amino acid sequence having at least 70% identity to the Brichos domain of a mammalian CTproSP-C have the capacity to decrease amyloid fibril formation and aggregation of Aβ-peptide.

According to a first aspect, the present invention provides an isolated protein selected from the group consisting of (i) proteins comprising an amino acid sequence having at least 70% identity to the C-terminal domain of lung surfactant protein C precursor (CTproSP-C) from human (SEQ ID NO: 2), bovine (SEQ ID NO: 5), rhesus (SEQ ID NO: 6), mouse (SEQ ID NO: 7), mink (SEQ ID NO: 8), rabbit (SEQ ID NO: 9) or rat (SEQ ID NO: 10), and (ii) proteins comprising an amino acid sequence having at least 70% identity to the Brichos domain of CTproSP-C from human (SEQ ID NO: 4), bovine (SEQ ID NO: 12), rhesus (SEQ ID NO: 13), mouse (SEQ ID NO: 14), mink (SEQ ID NO: 15), rabbit (SEQ ID NO: 16) or rat (SEQ ID NO: 17), for use as a medicament.

The term "% identity", as used throughout the specification and the appended claims, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). A comparison is made over the window corresponding to the shortest of the aligned sequences. The amino acid residues at each position are compared, and the percentage of positions in the query sequence that have identical correspondences in the target sequence is reported as % identity. The term "% similarity", as used throughout the specification and the appended claims, is calculated as described for "% identity", with the exception that the hydrophobic residues Ala, Val, Phe, Pro, Leu, Ile, Trp, Met and Cys are similar; the basic residues Lys, Arg and H is are similar; the acidic residues Glu and Asp are similar; and the hydrophilic, uncharged residues Gln, Asn, Ser, Thr and Tyr are similar. The remaining natural amino acid Gly is not similar to any other amino acid in this context.

Throughout this description, alternative embodiments according to the invention fulfill, instead of the specified percentage of identity, the corresponding percentage of similarity. Other alternative embodiments fulfill the specified percentage of identity as well as another, higher percentage of similarity, selected from the group of preferred percentages of identity for each sequence. For example, the isolated protein sequence may be 70% similar to another protein sequence; or it may be 70% identical to another sequence; or it may be 70% identical and furthermore 90% similar to another sequence.

Lung surfactant protein C(SP-C; SEQ ID NO: 3) is a hydrophobic, acylated transmembrane peptide having 35 amino acid residues. It is synthesized as proprotein of 197 amino acid residues (a 191 aa variant is present in certain species including human), lung surfactant protein C precursor (proSP-C; SEQ ID NO: 1). ProSP-C is expressed only in lung alveolar type II epithelial cells and is anchored in the endoplasmic reticulum (ER) membrane protein with its C-terminal in the ER lumen. ProSP-C undergoes proteolytic cleavages (see FIG. 1A), and the mature SP-C peptide corresponds to residues 24-58 of human proSP-C. SP-C and other protein and lipid components are secreted into the alveoli and are responsible for lowering the surface tension at the air/liquid interface, thereby preventing alveolar collapse at end expiration. As further illustrated in FIG. 1A, the processing of proSP-C also produces a C-terminal fragment, the C-terminal domain of lung surfactant protein C precursor (CTproSP-C; SEQ ID NOS: 2, 5-10; FIG. 1 B). The mature CTproSP-C protein corresponds to residues 59-197 of human proSP-C.

In certain embodiments, the isolated protein according to the present invention consists of less than or equal to 500, such as less than or equal to 250, such as less than or equal to 200, such as less than or equal to 150 amino acid residues. In certain embodiments, the isolated protein according to the present invention consists of more than or equal to 90, such as more than or equal to 100, such as more than or equal to 150 amino acid residues. A preferable size range is 90-200 amino acid residues, such as 100-150 amino acid residues.

SP-C (SEQ ID NO: 3) and hence also proSP-C (SEQ ID NO: 1) contain a transmembrane (TM) α-helix (corresponding to residues 9-34), composed only of valine, isoleucine and leucine (the "poly-Val" region"), with a high propensity to form β-strands. It is well conserved and lacks known homologous proteins. The discordant SP-C helix is consequently metastable in solution and can spontaneously convert into β-sheet aggregates and amyloid fibrils. SP-C fibrils have been observed in the alveoli of pulmonary alveolar proteinosis (PAP) patients, but not in healthy controls.

Furthermore, CTproSP-C (SEQ ID NO: 2) and hence also proSP-C (SEQ ID NO: 1) contain a domain known as the Brichos domain (CTproSP-C$_{Brichos}$; SEQ ID NO: 4), corresponding to residues 94-197 of human proSP-C (SEQ ID NO 1). Brichos domains contain about 100 amino acids and are found in several proteins associated with degenerative and proliferative diseases, such as Bri, associated with amyloid formation and familial British and Danish dementia, and CA11 associated with stomach cancer. It is also known that mutations in the Brichos domain are associated with lung disease, proSP-C misfolding and formation of intracellular aggregates. Elevated expression of proSP-C having a deletion of exon 4 (proSP-C$^{\Delta Exon4}$) produces a C-terminally shortened proprotein, resulted in lung dysmorphogenesis in transgenic mice and ER stress in transfected cells. Another mutation in the Brichos domain, resulting in the exchange of glutamine for leucine at position 188 in the proprotein (proSP-C$^{L188Q}$), is associated with dominantly inherited interstitial lung disease. Expression of the Brichos mutants proSP-C$^{\Delta Exon4}$ or proSP-C$^{L188Q}$ in lung-derived A549 cells or human embryonic kidney (HEK)293 cells results in increased formation of insoluble aggregates leading to apoptosis. In contrast, two other mutations, proSP-C$^{I73T}$ and proSP-C$^{E66K}$, localised in a region between the Brichos domain and the transmembrane domain (SP-C), are associated with altered intracellular trafficking but not aggregation. Thus, the Brichos domain in proSP-C and CTproSP-C is involved in prevention of (pro) SP-C aggregation. In one embodiment, the position corresponding to leucine-188 in human proSP-C is not glutamine. In a further embodiment, the position corresponding to leucine-188 in human proSP-C is strictly conserved. Obviously, the position corresponding to leucine-188 in human proSP-C has a different number in CTproSP-C (leucine-130 in human) and CTproSP-C$_{Brichos}$ (leucine-95 in human) as well as in certain other species, c.f. FIG. 1 B and SEQ ID NOS: 1-2 and 4-18.

CTproSP-C binds to the poly-valine part of non-helical SP-C, and this binding results in an increased helical content of the combined CTproSP-C/SP-C system. In particular, binding of recombinant human CTproSP-C to full-length non-helical SP-C results in α-helix formation of the SP-C.

Binding of recombinant human CTproSP-C to SP-C occurs via binding motifs found in the CTproSP-C Brichos domain (human proSP-C$^{94-197}$; SEQ ID NO: 4) and in the SP-C "poly-Val" region (SP-C$^{13-35}$) that contains hydrophobic residues (Val, Leu, Ile).

ProSP-C is also expressed in other mammalian species, and the corresponding SP-C and CTproSP-C cleavage products are provided. The corresponding CTproSP-C amino acid sequences from bovine, rhesus, mouse, mink, rabbit and rat are shown in SEQ ID NO 5-10. Their high degree of conservation (more than 70% identity) implicates functions in common with the human CTproSP-C, which in the native environment involve stabilizing SP-C and proSP-C, but as disclosed herein also encompass stabilizing Aβ protein. As shown herein, these two functions of CTproSP-C are structurally related, and the present invention thus encompasses proteins comprising an amino acid sequence having at least 70%, preferably at least 80%, preferably at least 90%, more preferably at least 95% identity to any mammalian CTproSP-C, specifically to CTproSP-C from human (SEQ ID NO: 2), bovine (SEQ ID NO: 5), rhesus (SEQ ID NO: 6), mouse (SEQ ID NO: 7), mink (SEQ ID NO: 8), rabbit (SEQ ID NO: 9) or rat (SEQ ID NO: 10); and preferably to CTproSP-C from human (human proSP-C$^{59-197}$; SEQ ID NO: 2).

The high degree of conservation of mammalian CTproSP-C (SEQ ID NO: 2, 5-10) is evident from FIG. 1 B, showing strictly conserved amino acid residues among known mammalian species ("Strict"; SEQ ID NO: 11). The conservation of these amino residues implicates a function of these amino acid residues in CTproSP-C. In a preferred embodiment, those amino acid residues of the isolated protein that correspond to the conserved amino acid residues among mammalian species are identical to the conserved amino acid residues, i.e. the isolated protein contains the defined amino acid residues of SEQ ID NO: 11. That is, in addition to the overall degree of identity/similarity to a certain CTproSP-C, those amino acid residues of the isolated protein that correspond to the conserved amino acid residues among mammalian species are identical to the conserved amino acid residues in this embodiment. Put another way, this embodiment implies that in the corresponding positions, the isolated protein having all conserved residues of mammalian CTproSP-C (SEQ ID NO: 11) contains all the following conserved residues of human CTproSP-C (SEQ ID NO: 2): His-1, Met-2, Ser-3, Gln-4, Lys-5, His-6, Thr-7, Glu-8, Met-9, Val-10, Leu-11, Glu-12, Met-13, Ser-14, Pro-18, Glu-19, Gln-21, Leu-24, Ala-25, Thr-32, Ala-34, Thr-35, Phe-36, Gly-39, Ser-40, Thr-41, Gly-42, Val-44, Asp-47, Tyr-48, Gln-49, Leu-51, Leu-52, Ala-54, Tyr-55, Lys-56, Pro-57, Ala-58, Pro-59, Gly-60, Thr-61, Cys-63, Tyr-64, Met-66, Lys-67, Ala-69, Pro-70, Ile-73, Pro-74, Ser-75, Leu-76, Glu-77, Ala-78, Arg-81, Lys-82, Gln-105, Gly-108, Gly-112, Ser-116, Phe-122, Leu-123, Gly-124, Val-127, Thr-129, Leu-130, Cys-131, Gly-132, Glu-133, Pro-135, Leu-136 and Tyr-138.

Another observation from the alignment of FIG. 1 B is that the conserved mammalian sequence contains gaps in relation to the sequence of individual mammalian species. It is therefore envisaged that an alignment of the isolated protein to e.g. the human CTproSP-C may contain some gaps, e.g. 0-5 gaps or 0-3 gaps. In human CTproSP-C, residues 88-93, 101-103 and 115 are missing in certain mammalian species, whereas one or more mammalian species have additional residues between residues 16-17 and 115-116 of human CTproSP-C. In one embodiment, one or more possible gaps may be present in SEQ ID NO: 11 at position 18, at position 89 to 94 and/or at position 116 to 118.

In one embodiment, the present invention encompasses proteins that are mammalian CTproSP-C proteins, specifically CTproSP-C proteins from human (SEQ ID NO: 2), bovine (SEQ ID NO: 5), rhesus (SEQ ID NO: 6), mouse (SEQ ID NO: 7), mink (SEQ ID NO: 8), rabbit (SEQ ID NO: 9) or rat (SEQ ID NO: 10); and preferably CTproSP-C from human (human proSP-C$^{59-197}$; SEQ ID NO: 2). The expression "CTproSP-C" refers in general to any mammalian CTproSP-C, and preferably to human CTproSP-C.

Furthermore, the Brichos domain of CTproSP-C has the same binding capacity as the full-length CTproSP-C. Accordingly, the present invention encompasses proteins comprising an amino acid sequence having at least 70%, preferably at least 80%, preferably at least 90%, and preferably at least 95%, identity to the Brichos domain of mammalian, preferably to the Brichos domain of human (SEQ ID NO: 2), bovine (SEQ ID NO: 5), rhesus (SEQ ID NO: 6), mouse (SEQ ID NO: 7), mink (SEQ ID NO: 8), rabbit (SEQ ID NO: 9) or rat (SEQ ID NO: 10) CTproSP-C, more preferably to the Brichos domain of human CTproSP-C (human proSP-C$^{94-197}$; SEQ ID NO:2).

In one embodiment, the present invention encompasses proteins that comprise the Brichos domain of mammalian, preferably the Brichos domain of human, bovine, rhesus, mouse, mink, rabbit or rat CTproSP-C, more preferably the Brichos domain of human CTproSP-C (human proSP-C$^{94-197}$; SEQ ID NO: 2). The expressions "the Brichos domain of proSP-C", "proSP-C$_{Brichos}$", "the Brichos domain of CTproSP-C" and "CTproSP-C$_{Brichos}$" refer in general to the Brichos domain of any mammalian proSP-C, and preferably to the Brichos domain of human proSP-C.

In one embodiment, the present invention encompasses proteins that are mammalian Brichos domains of CTproSP-C proteins, specifically Brichos domains of CTproSP-C proteins from human (SEQ ID NO: 4), bovine (SEQ ID NO: 12), rhesus (SEQ ID NO: 13), mouse (SEQ ID NO: 14), mink (SEQ ID NO: 15), rabbit (SEQ ID NO: 16) or rat (SEQ ID NO: 18); and preferably the Brichos domain of human CTproSP-C (human proSP-C$^{59-197}$; SEQ ID NO: 4).

The high degree of conservation of the Brichos domain of mammalian CTproSP-C (SEQ ID NO: 4, 12-17) is evident from FIG. 1 B, showing strictly conserved amino acid residues among known mammalian species ("Strict"; SEQ ID NO: 18). The conservation of these amino residues implicates a function of these amino acid residues in CTproSP-C$_{Brichos}$. In a preferred embodiment, those amino acid residues of the isolated protein that correspond to the conserved amino acid residues among mammalian species are identical to the conserved amino acid residues, i.e. the isolated protein contains the defined amino acid residues of SEQ ID NO: 18. That is, in addition to the overall degree of identity/similarity to a certain CTproSP-C$_{Brichos}$, those amino acid residues of the isolated protein that correspond to the conserved amino acid residues among mammalian species are identical to the conserved amino acid residues in this embodiment. Put another way, this embodiment implies that in the corresponding positions, the isolated protein having all conserved residues of the Brichos domain of mammalian CTproSP-C (SEQ ID NO: 18) contains all the following conserved residues of the Brichos domain of human CTproSP-C (SEQ ID NO: 4): Phe-1, Gly-4, Ser-5, Thr-6, Gly-7, Val-9, Asp-12, Tyr-13, Gln-14, Leu-16, Leu-17, Ala-19, Tyr-20, Lys-21, Pro-22, Ala-23, Pro-24, Gly-25, Thr-26, Cys-28, Tyr-29, Met-31, Lys-32, Ala-34, Pro-35, Ile-38, Pro-39, Ser-40, Leu-41, Glu-42, Ala-43, Arg-46, Lys-47, Gln-70, Gly-73, Gly-77, Ser-81, Phe-87, Leu-88, Gly-89, Val-92, Thr-94, Leu-95, Cys-96, Gly-97, Glu-98, Pro-100, Leu-101 and Tyr-103. In one embodiment, one or more possible gaps may be present in SEQ ID NO: 18 at position 53 to 58 and/or at position 80 to 82.

In one embodiment, the present invention encompasses proteins that are mammalian Brichos domains of CTproSP-C proteins, specifically Brichos domains of CTproSP-C proteins from human (SEQ ID NO: 4), bovine (SEQ ID NO: 12), rhesus (SEQ ID NO: 13), mouse (SEQ ID NO: 14), mink (SEQ ID NO: 15), rabbit (SEQ ID NO: 16) or rat (SEQ ID NO: 18); and preferably the Brichos domain of human CTproSP-C (human proSP-$C^{59-197}$; SEQ ID NO: 4).

In a specific embodiment, the isolated protein may contain the Brichos domain and a number of residues from the non-Brichos part of CTproSP-C. For instance, SEQ ID NO: 21 contains the Brichos domain of human CTproSP-C and eight additional amino acid residues from the non-Brichos part of human CTproSP-C. The function is maintained, but the resulting protein is more stable than the Brichos domain alone and can consequently be advantageous in providing a higher yield of non-aggregated protein.

Inside cellular membranes, polypeptides need to expose nonpolar side-chains and to hide the polar backbone. Consequently, only valine, isoleucine, leucine and phenylalanine promote insertion into the endoplasmic reticulum (ER) membrane and α-helix formation is an important part of the insertion process. ProSP-C is an integral ER membrane protein with a single α-helical transmembrane domain that consists of many valine and a few isoleucine and leucine, and this domain generates the mature SP-C (human SP-C, SEQ ID NO: 3). Due to the high β-sheet propensity of valine and isoleucine residues, it is also this characteristic that causes SP-C and proSP-C to be prone to form β-sheet polymers (amyloid fibrils), both in vitro and in living cells.

An endogenous anti-amyloid function exists, whereby the ER luminal, C-terminal domain of proSP-C (CTproSP-C), via unresolved mechanisms prevents the transmembrane segment of proSP-C and SP-C from aggregation into β-sheets. SP-C is highly conserved, lacks homologous proteins and its hydrophobic "poly-Val" region contains valine, isoleucine and leucine. However, the affinity of CTproSP-C is surprisingly not limited to these three hydrophobic amino acid residues. CTproSP-C recognizes five to seven residue segments with an unprecedented specificity. CTproSP-C binds to stretches of valine, isoleucine, leucine, phenylalanine, methionine or tyrosine, but not to alanine, tryptophan, glycine, proline or threonine counterparts. CTproSP-C thus binds to residues that promote membrane insertion according to the biological hydrophobicity scale (T Hessa et al, Nature 433, 377-381, 2005) and to tyrosine. The exception between the biological hydrophobicity scale and CTproSP-C substrate specificity, as revealed by binding to cellulose-bound peptides, is that CTproSP-C binds to a stretch of tyrosine. This may be explained by that tyrosine residues are exposed in CTproSP-C and bind the hydrophobic dye 1,1'-bis(4-anilino-5,5'-naphthalenesulfonate). Moreover, CTproSP-C binds exclusively to peptides in non-helical conformation.

The substrate specificity of CTproSP-C has similarities with the Hsp70 family chaperones BiP, which binds hydrophobic polypeptide segments after their translocation through the ER membrane, and DnaK. BiP recognizes 7-residue peptide segments with alternating patterns of hydrophobic residues, compatible with requirement of extended peptide structure for binding. However, valine is under-represented in peptides binding to BiP, while CTproSP-C does not bind to poly-Trp, the most favoured residue in BiP substrates. Likewise, the nature of the central five residues required for DnaK binding is similar to the substrate specificity of CTproSP-C, but the DnaK requirement for flanking basic residues is not seen for CTproSP-C.

Together, these data immediately suggest an explanation to the function of CTproSP-C; it prevents β-sheet aggregation by binding any part of the proSP-C candidate transmembrane segment that has not attained an α-helical, membrane-inserted, conformation. Targeting any short segment within the transmembrane domain of proSP-C would not be possible by recognition of a particular amino acid sequence.

In conclusion, CTproSP-C is an SP-C chaperone, and the native stabilizing, helix-promoting effect of CTproSP-C with respect to SP-C occurs via binding to the hydrophobic "poly-Val" region of SP-C (residues 13-35 of human SP-C, SEQ ID NO: 3), which contains mainly valine (10 residues), isoleucine and leucine, but not phenylalanine. In fact, the affinity of CTproSP-C for phenylalanine is to the best of our knowledge not previously known. Furthermore, the above CTproSP-C substrate specificity, per definition, implies that it can bind other candidate transmembrane segments that have failed to form compact, helical conformations which can be inserted into the membrane.

In contrast to SP-C, the target region of Aβ peptide (SEQ ID: 19) with a propensity for β-sheet formation is spanning residues 16-23 and contains two phenylalanine residues, but only one valine residue. It is therefore highly surprising that the isolated protein according to the invention has the capacity to decrease amyloid fibril formation and reduce aggregation of Aβ peptide. The CTproSP-C activity towards the amyloid β-peptide (A$β_{1-40}$; SEQ ID NO:19) associated with Alzheimer's disease has been experimentally evaluated herein.

Aβ is cleaved out from the TM segment of its precursor protein APP, aggregates into amyloid fibrils when released from the membrane, and contains regions, $L_{17}VFF_{20}$ (SEQ ID NO:22) and $I_{31}IGLMVGGW_{40}$ (SEQ ID NO:23) that, if they are in non-helical conformations, match the CTproSP-C substrate specificity. Indeed, CTproSP-C completely blocks amyloid fibril formation and aggregation of Aβ. The ability of CTproSP-C to catch an amyloidogenic polypeptide other than the transmembrane domain of proSP-C suggests that the properties it recognizes, namely sufficient hydrophobicity for membrane insertion and non-helical conformation, drive amyloid formation in general. This is in line with the observation that hydrophobicity and β-sheet propensity can be used to rationalize aggregation rates of amyloidogenic proteins. CTproSP-C is the first chaperone found to bridge recognition of unfolded transmembrane segments and amyloid prevention for proSP-C, SP-C and Aβ peptide.

Thus, the present invention in particular provides an isolated protein selected from the group consisting of (i) proteins comprising an amino acid sequence having at least 70% identity to the C-terminal domain of lung surfactant protein C precursor (CTproSP-C) from human (SEQ ID NO: 2), bovine (SEQ ID NO: 5), rhesus (SEQ ID NO: 6), mouse (SEQ ID NO: 7), mink (SEQ ID NO: 8), rabbit (SEQ ID NO: 9) or rat (SEQ ID NO: 10); and (ii) proteins comprising an amino acid sequence having at least 70% identity to the Brichos domain of CTproSP-C from human (SEQ ID NO: 4), bovine (SEQ ID NO: 12), rhesus (SEQ ID NO: 13), mouse (SEQ ID NO: 14), mink (SEQ ID NO: 15), rabbit (SEQ ID NO: 16) or rat (SEQ ID NO: 17), for use as a medicament in treatment of Alzheimer's disease, including dementia of the Alzheimer type, in a mammal, including man.

In specific embodiments, the treatment may be a preventive treatment. In other specific embodiments, the treatment may be a palliative treatment. In certain specific embodiments, the treatment may be a curative treatment.

According to another aspect, the present invention provides a pharmaceutical composition comprising a therapeutically effective amount of an isolated protein according to the invention and a suitable pharmaceutical carrier therefor. The pharmaceutical composition is useful in treatment of Alzheimer's disease, including dementia of the Alzheimer type, in a mammal, including man.

According to a related aspect, the present invention provides use of an isolated protein according to the invention for the manufacture of a medicament for the treatment of Alzheimer's disease, including dementia of the Alzheimer type, in a mammal, including man.

The isolated protein according to the invention can be incorporated into pharmaceutical compositions. Such compositions typically include the candidate compound and a suitable pharmaceutically acceptable carrier. As used herein, a "suitable pharmaceutical carrier" includes solvents, dispersion media, coatings, isotonic and absorption delaying agents, and the like, that are compatible with pharmaceutical administration. Supplementary active compounds can also be incorporated into the compositions.

A pharmaceutical composition is formulated to be compatible with its intended route of administration. Examples of routes of administration include parenteral (e.g., intravenous, intradermal, subcutaneous), oral, intranasal (e.g., inhalation), transdermal, transmucosal, intrathecal, intracerebral ventricular (e.g., using an Omaya reservoir-shunt with in-line filter that is surgically placed into the cisternal space), and rectal administration.

Potentially useful parenteral delivery systems for a composition include slow-dissolving polymer particles, implantable infusion systems, and liposomes. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene-diamine-tetra-acetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Treatment of Alzheimer's disease may also be effected by direct delivery of the isolated protein according to the invention to the central nervous system, preferentially to the brain.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating on particles of the isolated protein according the invention (e.g. lecithin), by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents in the composition. Examples of such agents include sugars, polyalcohols such as mannitol and sorbitol, and sodium chloride. Prolonged absorption of the injectable compositions can be brought about by including in the composition an agent which delays absorption, for example, aluminum monostearate or gelatin.

Sterile injectable solutions can be prepared by incorporating the isolated protein according to the invention in the required amount in an appropriate solvent with one or a combination of ingredients enumerated above, as required, followed by filtered sterilization. Generally, dispersions are prepared by incorporating the isolated protein according the invention into a sterile vehicle which contains a basic dispersion medium and the required other ingredients from those enumerated above. In the case of sterile powders for the preparation of sterile injectable solutions, the preferred methods of preparation are vacuum drying and freeze-drying, which yield a powder of the isolated protein according the invention plus any additional desired ingredient from a previously sterile-filtered solution thereof.

Oral compositions generally include an inert diluent or an edible carrier. For the purpose of oral therapeutic administration, the isolated protein according the invention can be incorporated with excipients and used in the form of tablets, troches, or capsules, e.g., gelatin capsules.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel®, or corn starch; a lubricant such as magnesium stearate or Sterotes®; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the isolated protein according the invention is formulated into ointments, salves, gels, or creams as generally known in the art.

The isolated protein according the invention can also be prepared in the form of suppositories (e.g., with conventional suppository bases such as cocoa butter and other glycerides) or retention enemas for rectal delivery.

In one embodiment, the isolated protein according the invention is prepared with a carrier that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions (including liposomes targeted to cells specifically affected by Alzheimer's disease with monoclonal antibodies) can also be used as pharmaceutically acceptable carriers. These can be prepared according to methods known to those skilled in the art.

It is advantageous to formulate oral or parenteral compositions in dosage unit form for ease of administration and uniformity of dosage. Dosage unit form as used herein refers to physically discrete units suited as unitary dosages for the subject to be treated, each unit containing a predetermined quantity of the isolated protein according the invention calculated to produce the desired therapeutic effect in association with the required pharmaceutical carrier.

Toxicity and therapeutic effects of the isolated proteins according to the invention can be determined by standard pharmaceutical procedures in cell cultures or experimental animals, e.g. for determining the $LD_{50}$ (the dose lethal to 50% of the population) and the $ED_{50}$ (the dose therapeutically effective in 50% of the population). Suitable animal models can be used such as those described for amyloidoses in Sturchler-Pierrat et al, Rev Neurosci, 10: 15-24, 1999; Seabrook et al, Neuropharmacol 38: 1-17, 1999; DeArmond et al, Brain Pathology 5: 77-89, 1995; Telling, Neuropathol Appl Neurobiol 26: 209-220, 2000; and Price et al, Science 282: 1079-1083, 1998.

The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to unaffected cells and thereby reduce side effects.

Data obtained from the cell culture assays and animal studies can be used in formulating a range of dosage for use in humans. The dosage of a compound lies preferably within a range of circulating concentrations that include the $ED_{50}$ with little or no toxicity.

The dosage may vary within this range depending upon the dosage form employed and the route of administration utilized. For any compound used in the method of the invention, the therapeutically effective dose can be estimated initially from cell culture assays in which, e.g., the rate of fibril formation or the rate of cell death is observed. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of an isolated protein according to the invention (i.e., an effective dosage) ranges from about 0.1 to 100 mg/kg body weight, more preferably about 1 to 100 mg/kg body weight, and even more preferably about 1 to 50 mg/kg body weight. The compound can be administered over an extended period of time to the subject, e.g., over the subject's lifetime. A dosage of 1 mg/kg to 100 mg/kg is usually appropriate, such as is the case for antibodies designated to act in the brain.

In some cases the compound can be administered once per week for between about 1 to 10 weeks, preferably between 2 to 8 weeks, more preferably between about 3 to 7 weeks, and even more preferably for about 4, 5, or 6 weeks. The compound can also be administered chronically. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments.

Recombinant isolated proteins according to the invention, including human CTproSP-C and its Brichos domain, for administration to mice expressing the human APP or to humans can be prepared in several ways. The recombinant proteins can be purified as described in Example 1. For increasing the likelihood of the proteins to pass the blood brain barrier (BBB) several methods are envisioned.

A couple of main strategies have emerged for drug passage through the BBB. They make use of endogenous transport systems, either by receptor-mediated transcytosis or by use of specific receptors, e.g. for glucose, amino acids or peptides. Peptides seem particularly attractive as vectors for carrying diverse cargos across the BBB. A number of different peptides have been shown to trigger endocytosis (typically by the LDL-receptor) and to be able to deliver a cargo across the BBB. Some of these peptides are amphiphilic positively charged cell penetrating peptides (CPPs, e.g. penetratin, ApoE derived peptide and other) but these can also be highly toxic at higher doses. Others like the synB family are also positively charged but without the hydrophobic part. A drawback of many of the endocytosis triggering peptides is that they, in order to be efficient, need be relatively large in order to form stable α-helices, which seems to correlate with efficient uptake. The advantage with delivery by transcytosis is that the cargo can be quite substantial and quite variable. A path where specific endogenous peptides, that have been shown to cross the BBB by a saturable transport system, would act as vectors for drug delivery is also a viable alternative. Several relatively short peptides of this kind, like MIF-1 (Pro-Leu-Gly, derived from oxytocin) and Peptide T (8 residues, derived from the HIV envelope) have been shown be efficiently transported across the BBB. See e.g., de Boer A G and Gaillard P J, Clin Pharmacokinet. 46:553-76, 2007; de Boer A G and Gaillard P J, Annu Rev Pharmacol Toxicol. 47:323-55, 2007; Pardridge W M, Drug Discov Today. 12:54-61, 2007, for descriptions of methods for delivery across the BBB. In the present case, it is envisioned that said peptides or proteins can be mixed with CTproSP-C or its Brichos domain, or alternatively they can be expressed covalently linked to CTproSP-C or its Brichos domain.

In other formulations, CTproSP-C or its Brichos domain can be linked to nanoparticles for delivery across the BBB (Lockman P R et al., Drug Dev Ind Pharm. 28: 1-13, 2002; Tosi G et al., Expert Opin Drug Deliv. 5:155-74, 2008).

Modifications such as lipidation can also be used to stabilize proteins and to enhance uptake and tissue penetration (e.g., into the brain). A method for lipidation of antibodies is described by Cruikshank et al, J Acquired Immune Deficiency Syndromes Hum Retroviral 14: 193, 1997.

When an isolated protein according to the invention is to be administered to an animal (e.g., a human) to treat Alzheimer's disease, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions of the invention can be included in a container, pack, or dispenser together with instructions for administration. For example, the instructions can include directions to use the composition to treat an individual having or at risk for Alzheimer's disease.

According to another aspect, the present invention provides a method of treating Alzheimer's disease, including dementia of the Alzheimer type, in a mammal, including man, in need thereof comprising administration to said mammal of a therapeutically effective amount of an isolated protein according to the invention or a pharmaceutical composition according to the invention.

In specific embodiments, the treatment may be a preventive treatment. In other specific embodiments, the treatment may be a palliative treatment. In certain specific embodiments, the treatment may be a curative treatment.

The present invention provides for both prophylactic and therapeutic methods of treating a subject at risk of (or susceptible to) Alzheimer's disease. As used herein, the term "treatment" is defined as the application or administration of an isolated protein according to the invention to a patient, or application or administration of an isolated protein according to the invention to an isolated tissue or cell line from a patient, who has Alzheimer's disease, a symptom of disease or a predisposition toward a disease, with the purpose to cure, heal, alleviate, relieve, alter, remedy, ameliorate, improve or affect the disease, the symptoms of disease or the predisposition toward disease.

In one aspect, the invention provides a method for preventing a disease or condition (i.e., decreasing the risk of contracting, or decreasing the rate at which symptoms appear that are associated with a disease or condition) associated with fibril formation caused by Aβ peptide by administering to the subject an isolated protein according to the invention that reduces aggregation and/or stabilizes the α-helical form of the polypeptide. Subjects at risk for Alzheimer's disease can be identified by, for example, any or a combination of appropriate diagnostic or prognostic assays known in the art. Administration of a prophylactic agent can occur prior to the manifestation of symptoms characteristic of the disease, such that the disease is prevented or, alternatively, delayed in its progression.

The isolated protein according to the invention can be administered to a patient at therapeutically effective doses to prevent, treat or ameliorate disorders involving fibril formation associated with Alzheimer's disease. A therapeutically effective dose refers to that amount of the compound sufficient to result in amelioration of symptoms of the disorders. Toxicity and therapeutic efficacy of such compounds can be determined by standard pharmaceutical procedures as described above.

It is also contemplated that the protein according to the invention can be administrated by gene therapy, such as by using expression vectors, plasmids or viruses to transfect cells in the neural system, preferably brain, such that the isolated protein is expressed by these cells in the central neural system. This is useful for the treatment of Alzheimer's disease.

The present invention will now be further illustrated by the following non-limiting examples.

EXAMPLES

Example 1

Expression and Isolation of Recombinant Human CTproSP-C$_{Brichos}$ (Human proSP-C$^{94-197}$; SEQ ID NO:4), Recombinant Human CTproSP-C (proSP-C$^{59-197}$; SEQ ID NO:2) and Recombinant Human CTproSP-C$^{L188Q}$ The CTproSP-C and CTproSP-C$^{L188Q}$ constructs were made as described in Johansson et al, J Biol Chem 281: 21032-21039, 2006. The CTproSP-C$_{Brichos}$ construct was amplified from the CTproSP-C construct and the following primers (DNA technology AIS, Aarhus, Denmark): 5'-GGTG CCATGGCTTTCTCCATCGGCTCCACT-3' (forward primer, SEQ ID NO:24) and 5'-CTCTAGAGGATCC GGATCCCTAGATGTAGTAGAGCGGCACCTCC-3' (reverse primer, SEQ ID NO:25); the underlined sequences are BamHI and NcoI cleavage sites, respectively. The amplified DNA fragment was digested with BamHI and NcoI and ligated into the expression vector pET-32c (Novagen, Madison, Wis.). This vector contains the coding regions for thioredoxin, hexahistidine and S-tags upstream of the insertion site.

For the expression of CTproSP-C and CTproSP-C$_{Brichos}$, transformed E. coli, strain Origami (DE3) pLysS (Novagen, Madison, Wis.) were grown at 37° C. in Luria-Bertani medium containing 100 µg/ml ampicillin for 16 h with constant stirring. The temperature was lowered to 25° C., and expression was induced at an OD600=1.1 by the addition of IPTG to 0.5 mM, and the bacteria were grown for another 4 h. The cells were then harvested by centrifugation at 6000×g for 20 min, incubated with lysozyme and DNase in 20 mM Tris-HCl, pH 8, 2 mM MgCl$_2$ and further loaded onto a Ni-NTA agarose column. The column was washed with 100 ml of 20 mM Tris, pH 8, and then with 20 ml of 20 mM Tris, pH 8, containing 20 mM imidazole. The target protein was then eluted with 150 mM imidazole in 20 mM Tris, pH 8. The eluted protein was dialyzed against 20 mM Tris, pH 8, where after thioredoxin and His tags were removed by cleavage with thrombin at an enzyme/substrate weight ratio of 0.002 for 3 h at 8° C. After this imidazole was added to a concentration of 15 mM and the solution was reapplied to a Ni-NTA agarose column to remove the released thioredoxin-His tag. CTproSP-C$^{L188Q}$ was expressed and purified as described earlier (Johansson et al, J Biol Chem 281:21032-21039, 2006). In brief, the protein was expressed as a fusion protein with thioredoxin/His$_6$/S-tag in E. coli. The protein was purified using immobilized metal affinity and ion exchange chromatography. Thrombin was used to remove the thioredoxin-tag and Hiss-tag. The protein purity was checked with SDS-PAGE and nondenaturing PAGE.

All resulting proteins are S-tagged, e.g. S-tagged human CTproSP-C (SEQ ID NO: 20). Unless otherwise specified, these S-tagged proteins have been used in the following examples.

Example 2

Analysis of CTproSP-C$_{Brichos}$, CTproSP-C and CTproSP-C$^{L188Q}$ Binding to SP-C Derived Peptide Spots on Cellulose Membranes SPOT membranes (Frank R, J Immunol Meth, 267:13-26, 2002), containing 10-residue fragments derived from SP-C (SP-C$^{I23V}$) were purchased from Sigma Genosys (Cambridge, England). The membranes were soaked in methanol for five min and then washed 3×30 min with T-TBS (50 mM Tris, 137 mM NaCl, 2.7 mM KCl, pH 8, containing 0.05% Tween) followed by incubation with 1 µg/ml CTproSP-C$_{Brichos}$, CTproSP-C or CTproSP-C$^{L188Q}$ in T-TBS for 1 h at 22° C. The membranes were then blocked with 2% BSA in TBS for one hour. After washing with T-TBS 4×1 h, the membranes were incubated with HRP-conjugated S-protein (Novagen, Madison, Wis.) diluted 1:5000 in T-TBS containing 2% BSA. The membranes were then washed again with T-TBS 4×1 h and binding was visualized by ECL according to the manufacturer's instructions.

As detailed above, 10-residue peptides with overlapping sequences corresponding to the entire SP-C$^{I23V}$ amino acid sequence (SEQ ID NO: 38) bound to cellulose membranes were probed for binding to CTproSP-C (SEQ ID NO: 4).

FIG. 2A shows binding of CTproSP-C to spots containing 10-residue fragments derived from SP-C$^{I23V}$. The peptide spots 1 to 25 cover the SP-C$^{I23V}$ sequence in an N- to C-terminal direction (see FIG. 2B) with exceptions of spot 8, 9, 11, 12, 17 and 18 (see below). Spot 7 contains the KRLLIV-VVVV (positions 11-20 in SP-C$^{I23V}$, SEQ ID NO:26) segment in SP-C$^{I23V}$, whereas spots 8 and 9 contain Leu-substituted (KRLLLLLLLL, SEQ ID NO:27) or Ala-substituted (KRAAAAAAAA, SEQ ID NO:28) versions thereof, respectively. In the same manner spots 10-12 contain RLLIV-VVVVV (positions 12-21 in SP-C$^{I23V}$, SEQ ID NO:29), RLLLLLLLLL (SEQ ID NO:30), and RAAAAAAAAA (SEQ ID NO:31), respectively, and spots 16-18 contain VVVVVLVVVV (positions 17-26 in SP-C$^{I23V}$, SEQ ID NO:32), LLLLLLLLLL (SEQ ID NO:33), and AAAAAAAAAA (SEQ ID NO:34), respectively. Spots 21 and 23 contain the same peptide (LVVVVIVGAL, positions 22-31 in SP-C$^{I23V}$, SEQ ID NO:35).

FIG. 2B displays a summary of CTproSP-C binding peptides along the SP-C$^{I23V}$ sequence. Dotted lines mark peptides to which CTproSP-C does not bind, while the solid lines represent peptides to which CTproSP-C binds. The underlined part of the SP-C$^{I23V}$ sequence corresponds to its transmembrane region. The numbering 1-35 refer to the mature SP-C peptide (SEQ ID NO: 3), the corresponding residues in proSP-C (SEQ ID NO: 1) are 24-58.

Thus, FIG. 2A-B show that binding motifs are found in the region that contains hydrophobic residues, i.e. peptides derived from the transmembrane "poly-Val" region of SP-C. Replacement of poly-Val motifs with poly-Leu results in no change in binding, compare spot pairs 7/8, 10/11 and 16/17, respectively, in FIG. 2A. In contrast, replacement of poly-Val with poly-Ala results in abolished binding, compare spots 7/9, 10/12 and 16/18, respectively, in FIG. 2A. The same peptide spot membranes as used for analysis of CTproSP-C substrate specificity were probed with CTproSP-C$_{Brichos}$ (proSP-C$^{94-197}$), which showed a binding profile very similar to that of CTproSP-C (proSP-C$^{59-197}$). As seen in FIG. 2C, the Brichos domain recapitulates the CTproSP-C binding properties. In contrast, CTproSP-C$^{L188Q}$ did not bind to any fragment of SP-C$^{I23V}$ (FIG. 2D). Thus, CTproSP-C and CTproSP-C$_{Brichos}$ have the same substrate specificity, while CTproSP-C$^{L188Q}$ shows abolished substrate binding.

Example 3

Substrate Specificity of CTproSP-C and its Brichos Domain

To study binding of recombinant human CTproSP-C and its Brichos domain to cellulose-bound decamers of the indicated residues, decamers of the indicated amino acid residues were covalently attached to a cellulose SPOT membrane (Frank R, J Immunol Meth, 267:13-26, 2002). Recombinant human S-tagged CTproSP-C (SEQ ID NO: 20) and the (S-tagged) Brichos domain of human CTproSP-C was produced in E. coli as described in Example 1.

The membrane was incubated with 1 µg/ml CTproSP-C in 50 mM Tris, 137 mM NaCl, 2.7 mM KCl, pH 8, containing 0.05% Tween (T-TBS) for 1 h at 22° C. After blocking with 2% BSA for one hour and washing with T-TBS 4×1 h, the membranes were incubated with HRP-conjugated S-protein (Novagen, Madison, Wis.) diluted 1:5000. The membranes were then washed again as above, and bound S-tagged CTproSP-C was visualized by enhanced chemiluminescence, see FIG. 3A. CTproSP-C binds to stretches of V, I, L, F, M, or Y, but not to A, W, G, P, or T counterparts. CTproSP-C thus binds to residues that promote membrane insertion according to the biological hydrophobicity scale and to Y. Mutant human CTproSP-C$^{L188Q}$, which does not bind SP-C and the ER-luminal part of the human Bri protein were used as controls, and both failed to bind to any of the membrane-bound peptides.

The binding capacity of human CTproSP-C was recapitulated by the Brichos region of human CTproSP-C (data not shown).

Example 4

Substrate Specificity of CTproSP-C

Figure 3:
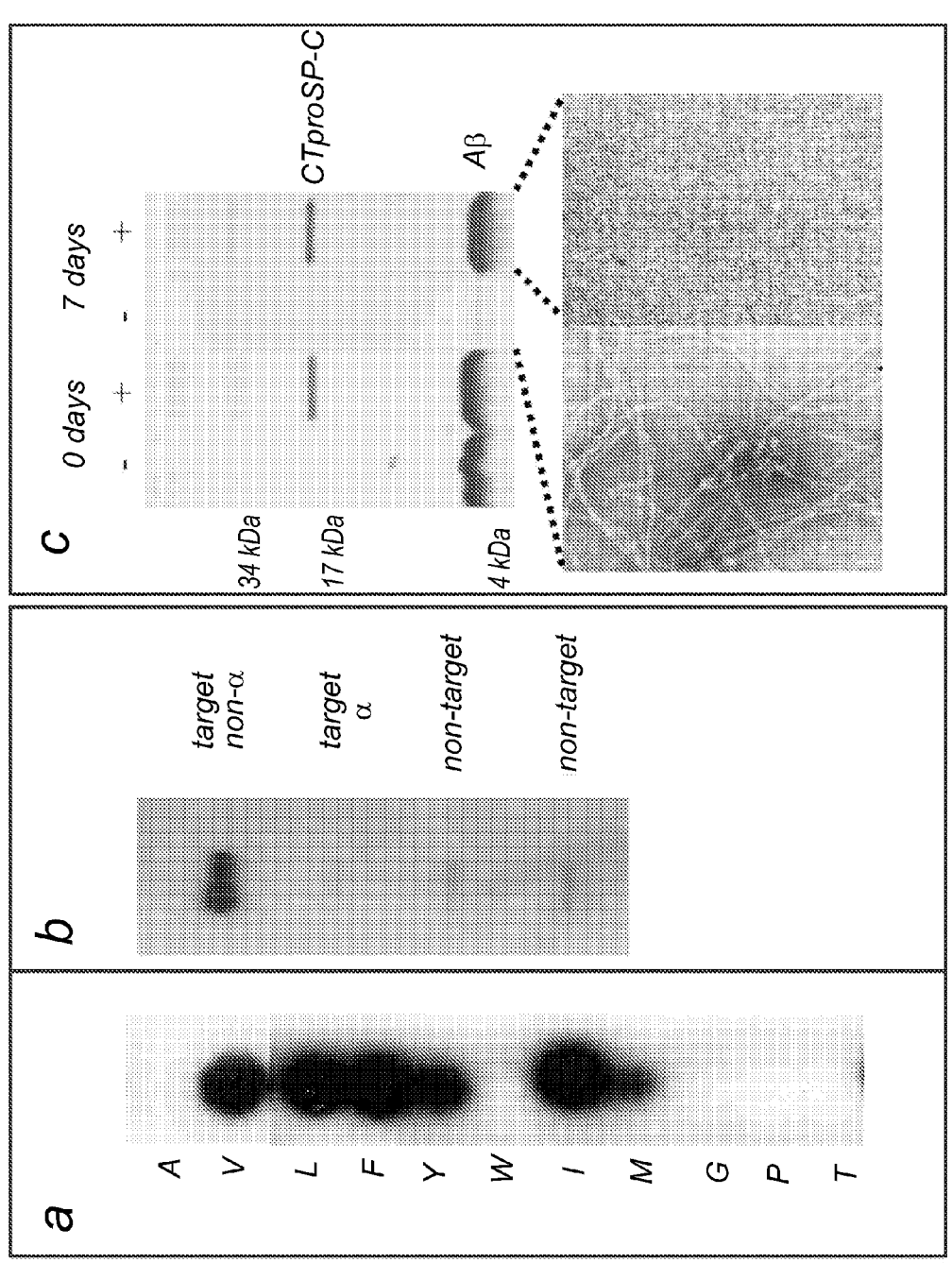
FIG. 3 panels A, B, and C show binding of CTproSP-C to peptide spots on cellulose membranes, SDS-PAGE of Aβ peptide samples and a transmission electron micrograph of Aβ peptide samples.

To study binding specificity of CTproSP-C, an LLLLLLL-LILLLILGALL (SEQ ID NO:36) peptide in non-helical (target, non-α, first lane) or in helical conformation (target, α, second lane), and a non-target peptide (third and fourth lanes) were covalently attached to a cellulose SPOT membrane (Frank R, J Immunol Meth, 267:13-26, 2002). For different conformations the peptide was blotted from 50% aqueous formic acid, in which the peptide is in β-strand conformation, or from ethanol, in which it is helical. To rule out the possibility that the different solvents caused artefactual binding of CTproSP-C, a non-target peptide (IPCCPV, SEQ ID NO:37) was adsorbed from 50% aqueous formic acid (third lane) or ethanol (fourth lane). Peptides were blotted on nitrocellulose membranes (Whatman, Germany) using a PR 648 Slot Blot filtration manifold (Amersham Biosciences, US). 1 µg/ml of recombinant human CTproSP-C was added and incubated at 22° C. for 2 h. The membrane was thereafter repeatedly washed with Tris-buffered saline, pH 7, and bound CTproSP-C was visualized by immunodetection and enhanced chemiluminescence as in Example 3. As seen in FIG. 3B, CTproSP-C binds exclusively to peptides in non-helical conformation.

Example 5

Anti-Amyloid Properties of CTproSP-C

Amounts of soluble $A\beta_{1-40}$ (25 µM) at start of experiment and after incubation for seven days at 37° C. alone (−) or with 2.5 µM CTproSP-C (+). The electron micrographs show abundant amyloid fibrils from Aβ alone and lack thereof for Aβ+CTproSP-C after six days of incubation. No fibrils were seen in any of the samples at start of experiment. The experiments were carried out with Aβ in 10 mM sodium phosphate buffer, pH 7.0, 150 mM sodium chloride, after dilution of Aβ from a stock solution in DMSO. $A\beta_{1-40}$ was incubated with and without 2.5 µM CTproSP-C at 37° C. under agitation.

At start of experiment and after seven days, samples were removed to determine the level of aggregation. The samples were centrifuged for 6 min at 16000×g, the supernatants were removed and centrifuged for another 2 min at 16000×g. The supernatant from the last centrifugation was then analysed by SDS-PAGE on 10-16% Tris-Tricine gels under non-reducing conditions and stained with Coomassie. For electron microscopy, aliquots of 2 µl were adsorbed for 1 min on 200-mesh copper grids and stained with 2% uranyl acetate for 30 s before being examined and photographed using a Hitachi H7100 microscope operated at 75 kV.

The resulting SDS-PAGE gels and photographs are shown in FIG. 3C. It is evident that CTproSP-C completely blocks amyloid fibril formation and aggregation of Aβ in vitro.

Example 6

CTproSP-C Prevents Fibril Formation of $A\beta_{1-40}$ $A\beta_{1-40}$ (SEQ ID NO: 19) was purchased from Bachem (Germany) and stored in a lyophilized state at −70° C. until use. To promote monomeric starting solutions, the peptide was dissolved, vortexed and sonicated at 1 mg/ml in dimethylsulfoxide (DMSO) before dilution in working buffer.

Human recombinant CTproSP-C was expressed and purified as described in Example 1 (SEQ ID NO: 20).

$A\beta_{1-40}$ aggregation and fibril formation experiments were carried out with an Aβ concentration of 25 µM in 10 mM sodium phosphate buffer, pH 7.0, 150 mM sodium chloride, containing 10% (v/v) DMSO. $A\beta_{1-40}$ was incubated with and without 25 and 2.5 µM CTproSP-C at 37° C. under agitation. At various time points, samples were removed to determine the level of aggregation. The samples were centrifuged for 6 min at 16000×g, the supernatants were removed and centrifuged for another 2 min at 16000×g. The supernatant from the last centrifugation was then analysed by SDS-PAGE on 10-16% Tris-Tricine gels under non-reducing conditions and stained with Coomassie. As controls $A\beta_{1-40}$ was incubated with 2.5 µM chicken cystatin (MW 13.3 kDa) or human antithrombin (MW 58 kDa) in the same manner as described above.

To determine the extent of fibril formation, $A\beta_{1-40}$ was incubated as described above with or without 2.5 µM CTproSP-C, as well as with 25 µM chicken cystatin or bovine serum albumin. After 6 days the samples were removed and analysed by transmission electron microscopy (TEM), see below.

In order to investigate the ability of CTproSP-C to dissociate already formed fibrils, 25 µM $A\beta_{1-40}$ was incubated for 6 days at 37° C. with shaking, the presence of fibrils was verified by TEM, and thereafter CTproSP-C was added to a final concentration of 25 µM. The samples were incubated further for 1 to 7 days and thereafter the amount of fibrils was again estimated using TEM.

For each sample, aliquots of 2 µl were adsorbed for 1 min on 200-mesh copper grids and stained with 2% uranyl acetate for 30 s before being examined and photographed using a Hitachi H7100 microscope operated at 75 kV.

Figure 4:
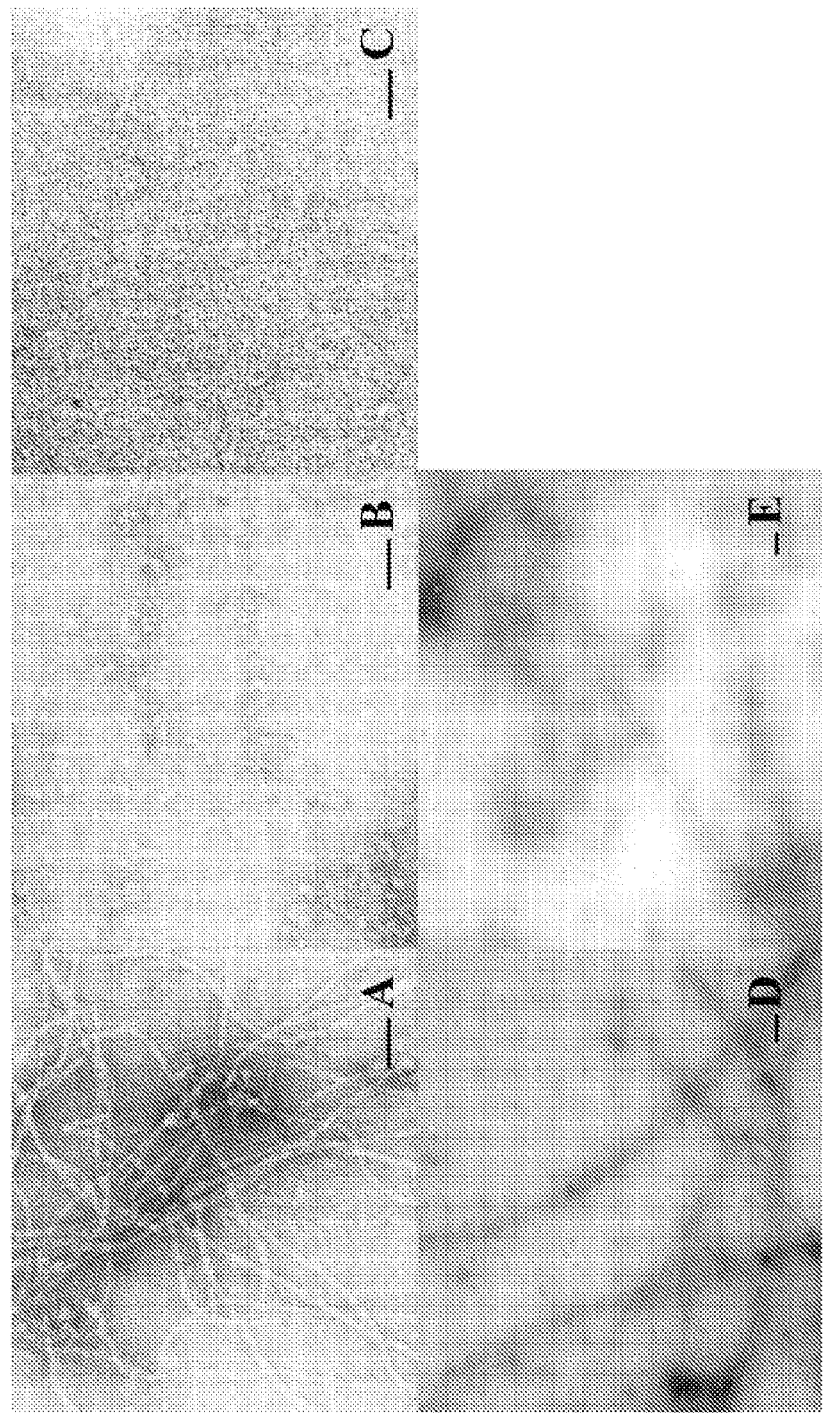
FIG. 4 panels A, B, C, D, and E show transmission electron micrographs of Aβ peptide samples.

$A\beta_{1-40}$ was incubated in the presence and absence of CTproSP-C at 1:1 and 10:1 molar ratios. TEM images obtained after 6 days of incubation are shown in FIG. 4. Briefly, FIG. 4 shows transmission electron micrographs of 16000×g pellets formed from 25 µM $A\beta_{1-40}$ incubated at 37° C. in 10 mM sodium phosphate buffer, pH 7.0, 150 mM sodium chloride with 10% DMSO (v/v) alone (A), together with 25 µM of CTproSP-C (B), 2.5 µM of CTproSP-C(C), 25 µM BSA (D) or 25 µM chicken cystatin (E). Scalebar=100 nm.

The TEM images obtained after 6 days of incubation show that fibril formation of $A\beta_{1-40}$ (FIG. 4A) was completely abolished in the presence of CTproSP-C, even at less than equimolar ratios (FIG. 4B-C). Neither chicken cystatin, nor BSA in equimolar amounts relative to $A\beta_{1-40}$ prevented $A\beta_{1-40}$ fibril formation (FIG. 4D-E), indicating specificity of the interaction between CTproSP-C and $A\beta_{1-40}$.

Pre-formed amyloid fibrils of $A\beta_{1-40}$ were incubated with CTproSP-C at a 1:1 molar ratio relative to the $A\beta_{1-40}$ concentration used to form the fibrils. No change in the amount or appearance of fibrils observed by TEM was seen after up to 7 days incubation with CTproSP-C (data not shown). These experiments indicate that CTproSP-C does not have the ability to dissociate already formed fibrils, but rather interacts with species on the pathway to fibril formation.

Example 7

CTproSP-C Prevents Aggregation of $A\beta_{1-40}$ $A\beta_{1-40}$ was incubated with CTproSP-C as well as the control proteins chicken cystatin or human antithrombin at an $A\beta$/protein molar ratio of 10:1. After 7 days, the amounts of soluble $A\beta_{1-40}$ after centrifugation at 16000×g was analysed by SDS-PAGE.

Figure 5:
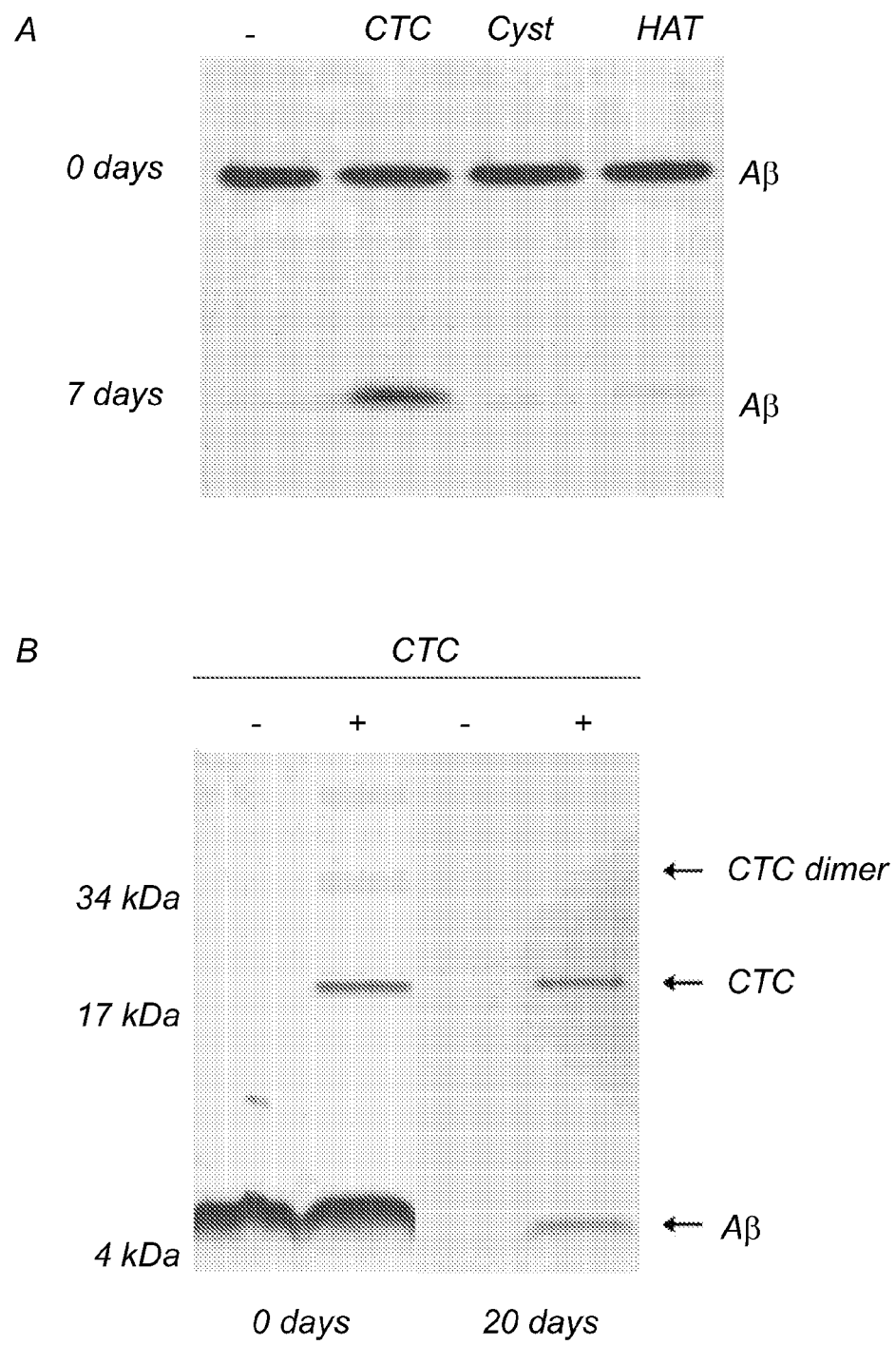
FIG. 5 panels A and B show SDS-PAGE of soluble Aβ peptide fractions incubated with or without CTproSP-C.

FIG. 5 shows SDS-PAGE of 16000×g soluble fractions of (A) 25 µM $A\beta_{1-40}$ incubated for 0 and 7 days in 10 mM sodium phosphate buffer, pH 7.0, 150 mM sodium chloride with 10% DMSO (v/v) in the presence or absence of 2.5 µM of CTproSP-C (CTC), Chicken cystatin (Cyst) or human antithrombin (HAT); and (B) 25 µM $A\beta_{1-40}$ incubated for 0 or 20 days in 10 mM sodium phosphate buffer, pH 7.0, 150 mM sodium chloride with 10% DMSO (v/v) in the presence or absence of 2.5 µM of CTproSP-C.

The amounts of $A\beta$ at t=0 were equal for all mixtures, but after 7 days no $A\beta$ were seen from the samples with $A\beta$ alone or co-incubated with chicken cystatin. Minute amounts of soluble $A\beta$ were seen in the sample co-incubated with antithrombin, while the sample containing CTproSP-C showed almost equal amounts of soluble $A\beta$ as seen at t=0 (FIG. 5A). Even after 20 days of co-incubation of CTproSP-C and $A\beta$, soluble $A\beta$ was found (FIG. 5B).

As seen in FIG. 5, CTproSP-C is able to keep $A\beta$ in a soluble state for up to 20 days, and the inability of control proteins of similar size to do so further indicates that the CTproSP-C effect is based on specific interactions.

Example 8

CTproSP-C Prevents Aggregation of $A\beta_{1-40}$ $A\beta_{1-40}$ was dissolved in DMSO to a concentration of 231 µM and diluted to a concentration of 25 µM with or without 25 µM CTproSP-C in 50 mM ammonium acetate buffer, pH 7.0. A sample from each mixture was immediately taken for MALDI analysis. The solutions were then incubated at 37° C. for two days with agitation and thereafter for additionally four days at 22° C. without shaking.

For matrix-assisted laser desorption ioisation (MALDI) analysis, the samples were diluted in 30% acetonitrile with 0.1% trifluoroacetic acid (TFA) to an $A\beta_{1-40}$ concentration of 4 µM, and 0.5 µl of each sample was mixed with 0.5 µl of a 0.8 µM somatostatin in 30% acetonitrile, 0.1% TFA. The mixture was applied on top of a layer of sinapinic acid pre-crystallized on the MALDI target plate from a 20 mg/ml solution in acetone, and co-crystallised with 1 µl of sinapinic acid (20 mg/ml) dissolved in 50% acetonitrile, 0.1% TFA. Data between 2000 and 10000 mass to charge ratio (m/z) were acquired on a Bruker Autoflex (Bruker Daltonics, Billerica, Mass.) mass spectrometer operated in linear mode employing delayed extraction. 1000 shots were automatically acquired for each sample; for 50 different locations, batches of 20 laser shots per position were averaged using a pre-defined shooting pattern.

An inhibitory effect on $A\beta_{1-40}$ aggregation by CTproSP-C was evident when 25 µM $A\beta_{1-40}$ was incubated with or without equimolar amounts of CTproSP-C at 37° C. for two days with agitation and additionally for four days at 22° C. The samples were analysed for the presence of monomeric, soluble $A\beta_{1-40}$ by MALDI MS, using somatostatin as an internal non-aggregating standard to obtain reliable concentration estimates for peptides. Automatic collection from several different points for each MALDI target was employed in order to minimize human errors and biases.

Figure 6:
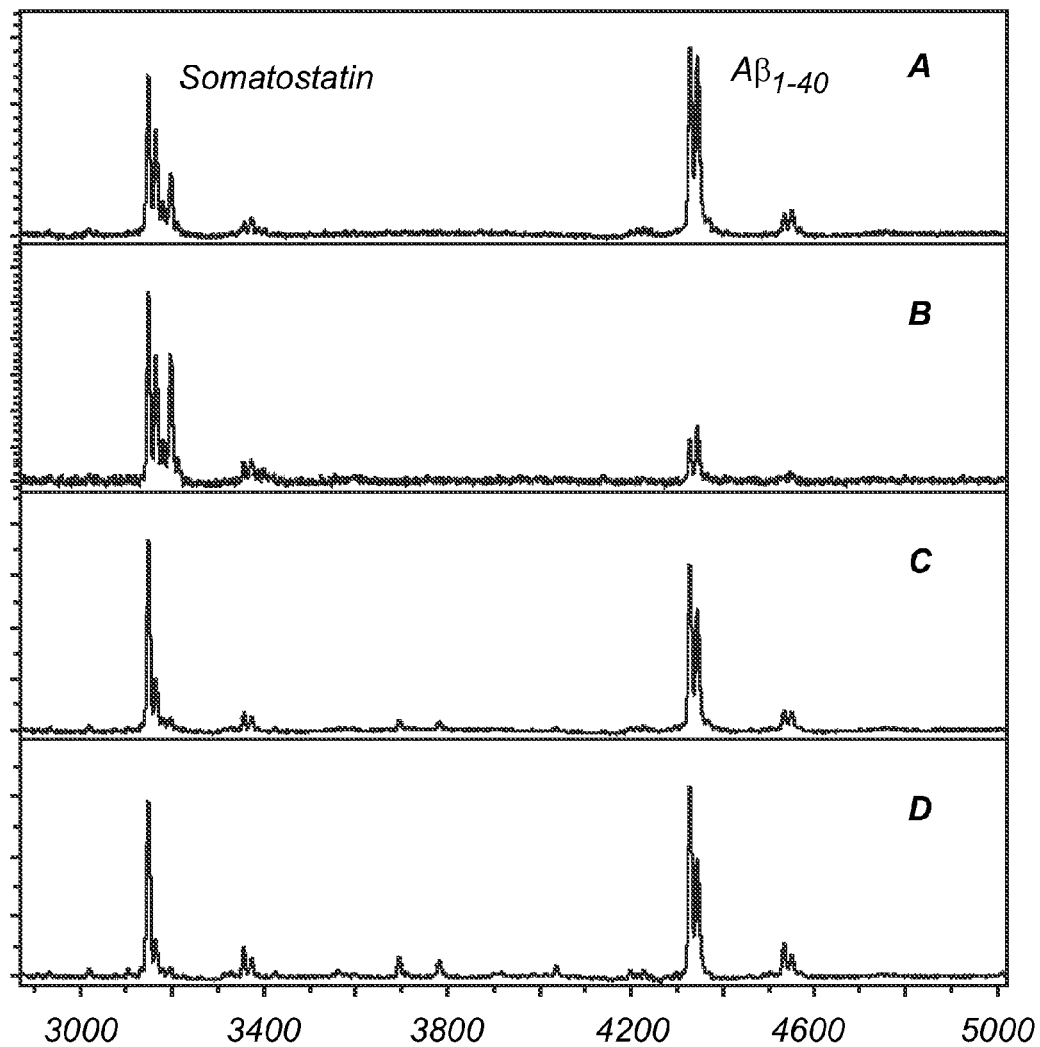
FIG. 6 panels A, B, C, and D show MALDI-MS graphs for Aβ peptide alone or in the presence of CTproSP-C.

FIG. 6 shows the quantification of $A\beta_{1-40}$ (theoretical mass 4329.86 Da) in solution assessed by MALDI MS using somatostatin (theoretical mass 3149.61 Da) as an internal standard. Panels (A) and (B) show 25 µM of $A\beta_{1-40}$ alone, while (C) and (D) show 25 µM of $A\beta_{1-40}$+25 µM CTC. Samples in (A) and (C) were analysed before incubation, and samples in (B) and (D) were analysed after incubation for 2 days at 37° C. with agitation and for additionally 4 days at 22° C. in 50 mM ammonium acetate buffer, pH 7.0.

Using this method, a good correlation between somatostatin and $A\beta_{1-40}$ concentrations was obtained ($R^2>0.9$). $A\beta_{1-40}$ incubated alone showed 80% decrease in soluble peptide relative to somatostatin (FIGS. 6A and 6B), whereas in the samples containing both $A\beta_{1-40}$ and CTproSP-C, the amount of soluble $A\beta_{1-40}$ remained constant over the time period analysed (FIGS. 6C and 6D). Thus, MALDI mass spectrometry confirms that CTproSP-C has an inhibitory effect on aggregation of $A\beta_{1-40}$, i.e. keeps $A\beta_{1-40}$ in a soluble, monomeric state.

Example 9

Interaction Studies of CTproSP-C and $A\beta_{1-40}$ Using Size-Exclusion Chromatography (SEC) and Immunoblot Analysis SEC coupled with immunoblotting was employed to study the interaction between $A\beta_{1-40}$ and CTproSP-C. SEC was performed on a Superdex® 200 column (Amersham Biosciences, Uppsala, Sweden) attached to an FPLC instrument (Amersham Biosciences). The column was equilibrated with 10 mM sodium phosphate buffer pH 7.0, 150 mM sodium chloride and absorbance at 214 nm was recorded. The column was initially calibrated with fibrinogen (340 kDa), aldolase (158 kDa), bovine serum albumin (67 kDa) and chicken cystatin (13.3 kDa).

For the interaction study three different samples; (i) 34 µM $A\beta_{1-40}$, (ii) 34 µM CTproSP-C and (iii) 34 µM of both $A\beta_{1-40}$ and CTproSP-C, were prepared in 10 mM sodium phosphate buffer, pH 7.0, 150 mM sodium chloride, 10% (v/v) DMSO. All samples were applied to the column directly after preparation and eluted at a flow rate of 0.7 ml/min using the same buffer as for equilibration. Fractions of 1.2 ml were collected from all runs and 100 µl/fraction were blotted on nitrocellulose membranes (Whatman, Germany) using a PR 648 Slot Blot filtration manifold (Amersham Biosciences, US).

For samples containing both Aβ$_{1-40}$ and CTproSP-C, two sets of blots were analysed, to allow detection of both peptides. For detection of Aβ$_{1-40}$, the membranes were boiled in phosphate buffered saline (PBS), pH 7.4, for five minutes and allowed to cool in TBS-Tween (0.1%) before blocking with 5% non fat dry milk. The membranes were probed with the monoclonal antibody 4G8 (1:2000, Signet, UK) followed by anti-mouse HRP-conjugated secondary antibody (1:5000, GE Healthcare, UK). For detection of S-tagged CTproSP-C, the membranes were blocked with 5% non fat milk and probed with HRP-conjugated S-protein (1:5000, Novagen, US). Enhanced chemiluminescence (Millipore) was used to detect antibody binding in both cases. Image J was used to measure the intensity of the spots.

Figure 7:
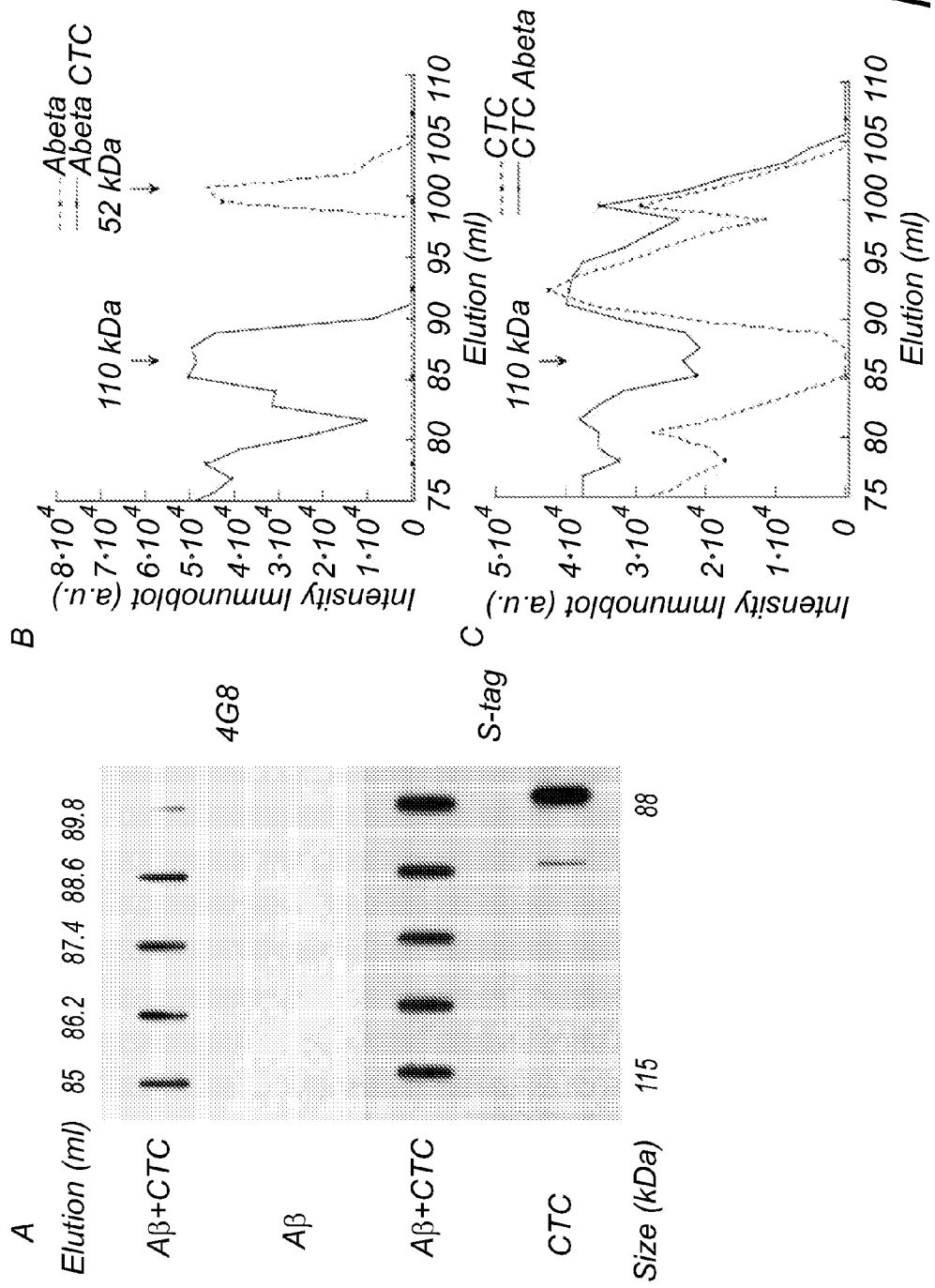
FIG. 7 panels A, B, and C show immunoblot analyses of SEC fractions of Aβ and Aβ+CTproSP-C, probed with the antibody 4G8 or S-protein.

FIG. 7 shows immunoblot analyses of SEC fractions of Aβ and Aβ+CTproSP-C ("CTC"), probed with the antibody 4G8 or S-protein. FIG. 7A shows immunoblot analyses of SEC fractions corresponding to elution volumes 85-89 ml. The polypeptide contents in the samples applied to the column are indicated to the left. Upper two rows were probed with the antibody 4G8, recognizing Aβ$_{1-40}$, and the two lower rows were probed with S-protein for detection of S-tagged CTproSP-C (SEQ ID NO: 20). FIGS. 7B and 7C show intensities of immunoblots of SEC fractions (elution volume 75-110 ml) probed with the antibody 4G8 (B) or S-protein (C). The samples containing Aβ+CTproSP-C are represented by solid lines, while Aβ alone (B) and CTproSP-C alone (C) are represented by dotted lines. The arrows mark molecular masses estimated from elution positions of proteins with known masses. The figure is representative of three independent runs.

The 214 nm absorbance profile for Aβ$_{1-40}$ showed a pattern compatible with the presence of low-number oligomeric species and a small amount of larger species eluting in the void volume (not shown), indicating the presence of pre-fibrillar soluble oligomers.

In the Aβ$_{1-40}$+CTproSP-C sample, the larger Aβ were absent, which further supports the results from the aggregation assays. CTproSP-C on its own appeared as two groups of oligomers. The clearly dominating peak eluted at a position corresponding to the size of trimers to pentamers, and another peak eluted at a position corresponding to dodecamers. This result is in good agreement with analytical ultracentrifugation and ESI mass spectrometry data showing that CTC trimers and oligomers thereof are the main species (C Casals et al, FEBS J, 275:536-547, 2008).

The absorbance profile for SEC of Aβ$_{1-40}$+CTproSP-C showed that the peak corresponding to CTproSP-C trimers to pentamers increased about 30% compared to the elution of CTproSP-C alone, which suggests that Aβ binds to and stabilises CTproSP-C trimer-pentamers. No unique peak corresponding to an Aβ/CTproSP-C complex could be detected by absorbance measurements, possibly due to the comparatively large elution volume of CTproSP-C alone. SEC of a mixture of Aβ$_{1-40}$ and CTproSP-C followed by dot blot analysis of fractions, however, clearly showed a unique peak compared to the polypeptides alone (FIG. 7). This indicates that Aβ and CTproSP-C interact and form a stable complex. The new peak observed corresponds to a complex of about 110 kDa and was accompanied by a loss of the Aβ peak corresponding to ~52 kDa (FIGS. 7B and C). Suggestively, the new species could thus be a 12-mer of Aβ$_{1-40}$ (52 kDa) bound to a trimer of CTC (55 kDa).

SEC thus shows that the two molecules interact and form complexes that are stable during chromatography. It appears that the complexes formed are composed of a CTproSP-C trimer interacting with an Aβ 12-mer. These findings are compatible with the existence of Aβ oligomers, possibly micellar-like structures that are able to stay intact during SEC and SDS-PAGE and to associate with CTproSP-C.

Example 10

Interaction Studies of CTproSP-C and Aβ$_{1-40}$ Using Electrospray Ionization Mass Spectrometry (ESI-MS)

To further study Aβ/CTproSP-C complex formation, a mixture of Aβ$_{1-40}$ and CTproSP-C as well as the separate polypeptides were analysed using ESI mass spectrometry.

CTproSP-C (theoretical average molecular weight 18264.89 Da) stored at a concentration of 1.1 mM at −20° C. in 20 mM sodium phosphate buffer, pH 7.0, 30 mM sodium chloride, was diluted to 10 µM in 10 mM ammonium acetate buffer, pH 6.9, for analysis alone. Aβ$_{1-40}$ (theoretical average molecular weight 4329.9 Da) was dissolved in 10 mM ammonium bicarbonate buffer, pH 10.8, with 1% (v/v) ammonia, to an Aβ concentration of 100 µM and stored at −20° C. prior to use. When CTproSP-C and Aβ$_{1-40}$ were analysed together, a mixture of 10 µM CTC and 50 µM Aβ$_{1-40}$ was prepared in 10 mM ammonium bicarbonate buffer with a final pH of 7-8.

Data were acquired on a QTOF Ultima API mass spectrometer, (Waters, Milford, Mass.) equipped with a Z-spray source, operated in the positive-ion mode under the control of the MassLynx 4.1 program, between 1000-5000 m/z with 2 sec per scan and an inter-scan interval of 0.1 seconds. Samples were introduced via a nanoflow electrospray interface from metal-coated borosilicate glass capillary needles (Proxeon Biosystems, Odense, Denmark), and the source temperature was set to 80° C. Spraying conditions were tuned with a capillary voltage between 1.2 and 1.9 kV, and cone and RF lens energies were 100 and 38 V, respectively. The pumping of the ES interface region was restricted, bringing the reading on the backing pirani vacuum gauge up from 1.8 to 1.95 mbar and employing an analyser pressure of $5.85 \times 10^{-5}$ mbar with the use of argon as collision gas. In MS mode the collision voltage was set to 10 V, and in MS/MS mode CTproSP-C/Aβ$_{1-40}$ complexes were disrupted by increasing the collision voltage to 80 V. The instrument was operated in V-mode (single reflector mode) at a resolution of 10,000 (FWHM definition), and the mass scale was calibrated against PEG-3400.

Figure 8:
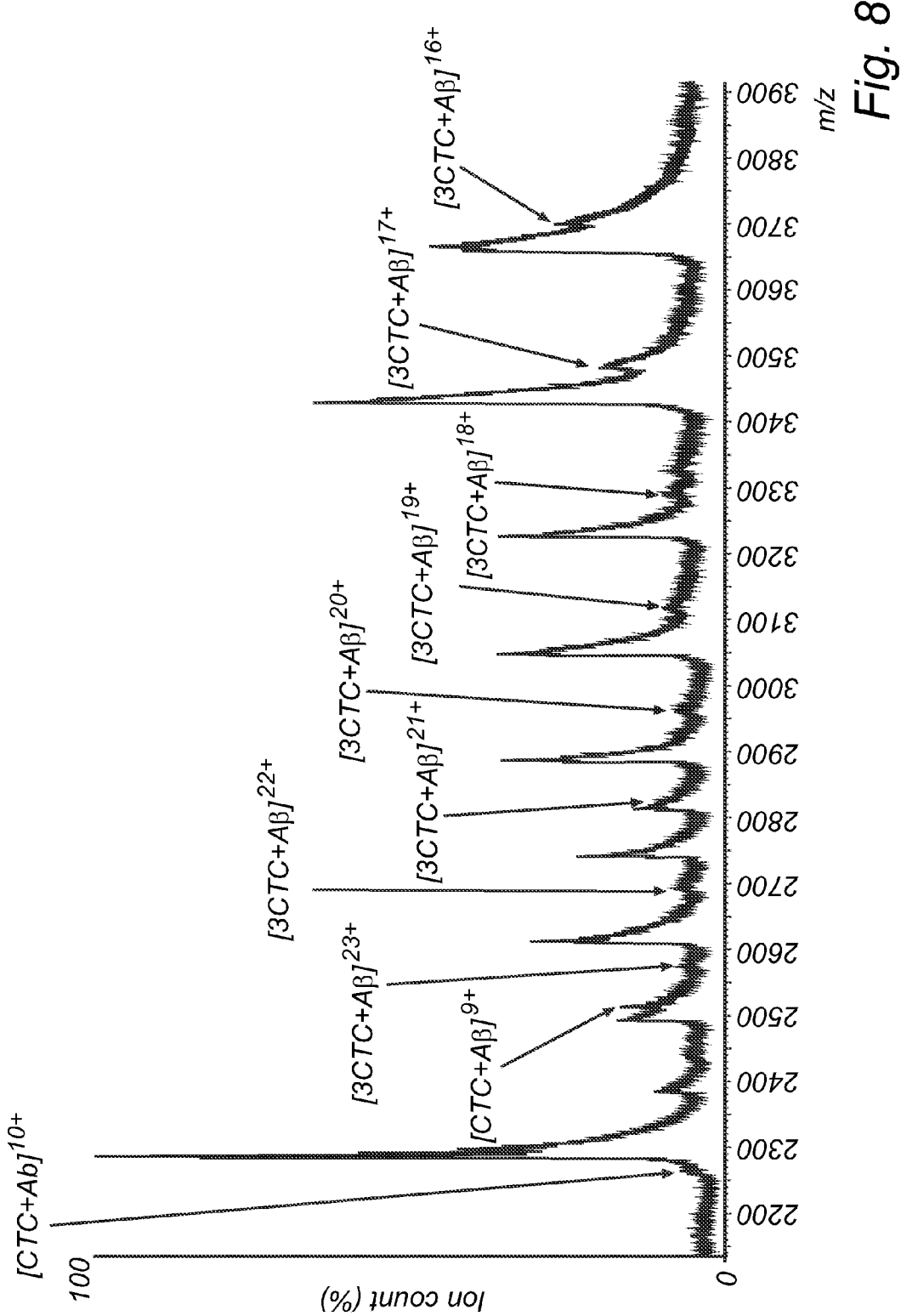
FIG. 8 shows a nano-spray ESI-MS spectrum of CTproSP-C mixed with Aβ in ammonium bicarbonate buffer.

FIG. 8 shows a nano-spray ESI-MS spectrum of 10 µM CTproSP-C (CTC) mixed with 50 µM Aβ$_{1-40}$ in 10 mM ammonium bicarbonate buffer, pH 7-8. Labelled peaks correspond to heteromers of CTproSP-C and Aβ$_{1-40}$ with different charge states, as deduced from spectra of CTC or Aβ$_{1-40}$ alone.

Comparison of the peak pattern obtained from the individual peptides and the mixed sample indicated formation of complexes between Aβ$_{1-40}$ and CTproSP-C. CTproSP-C oligomers were found (FIG. 8, peaks not annotated). For the mixture, several peaks not corresponding to homomers of CTproSP-C or Aβ, but that could instead be assigned to heteromers of CTproSP-C/Aβ appeared (FIG. 8). Peaks of low signal intensity corresponding to one CTproSP-C bound to one Aβ$_{1-40}$ with nine (m/z 2511) or ten (m/z 2260) charges were found. A complete charge state envelope with 16-23 charges (m/z 3696 to 2572) corresponding to a trimer of CTproSP-C in complex with one Aβ$_{1-40}$ peptide was observed.

Figure 9:
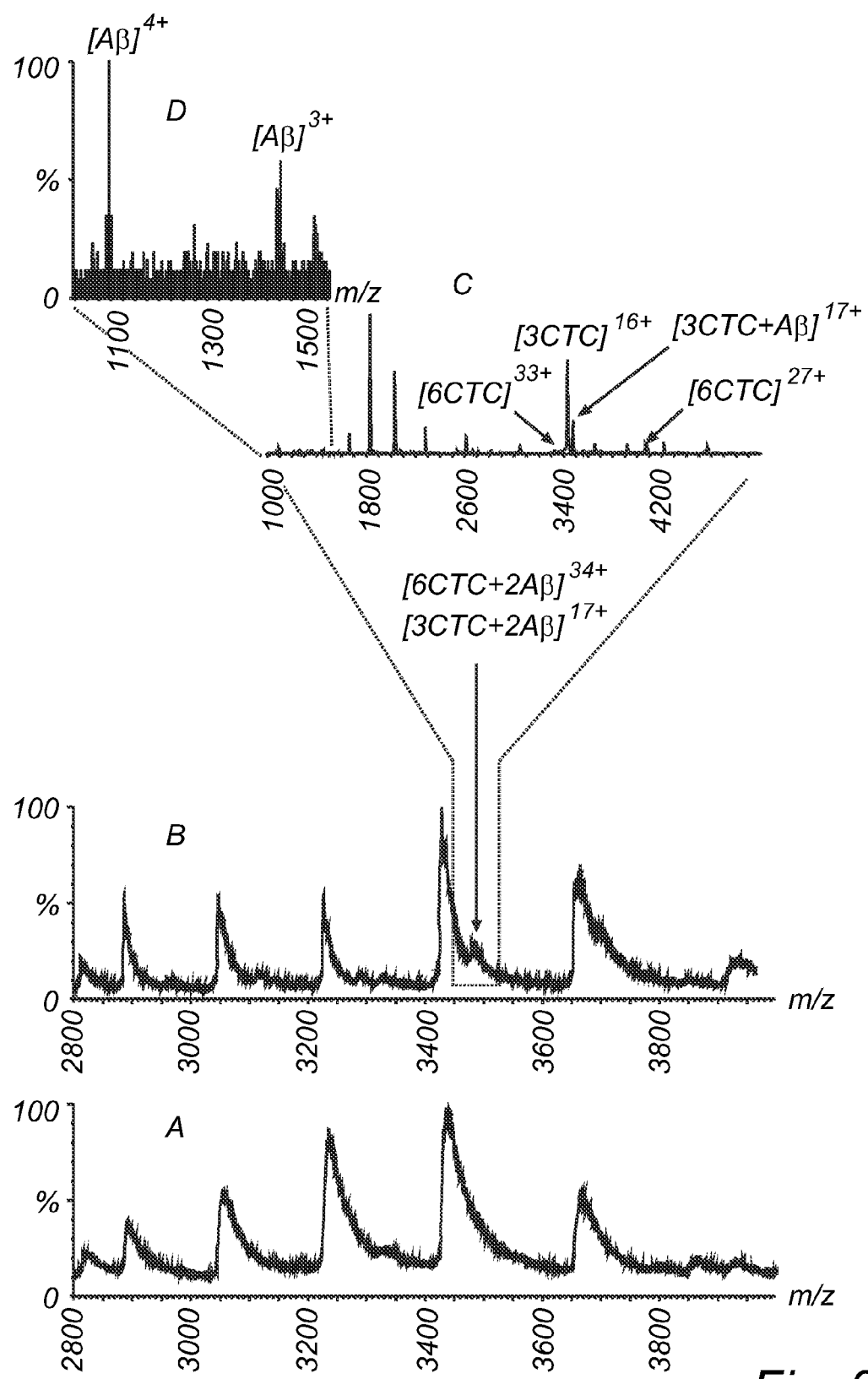
FIG. 9 panels A, B, C, and D show nano-spray ESI-MS spectra of CTproSP-C and a mixture of CTproSP-C and Aβ, together with an MS/MS spectrum of the mixture.

The peak at m/z 3485 (FIG. 8), not found in the spectrum of CTproSP-C alone, and corresponding to [3CTproSP-C+Aβ]$^{17+}$ was selected for MS/MS to verify that it represents a complex of the two peptides, i.e. by disruption of the CTproSP-C/Aβ complex by MS/MS. FIG. 9 shows a nanospray ESI-MS spectrum of (A) 10 μM CTproSP-C(CTC) in 10 mM ammonium bicarbonate buffer, pH 7-8 and (B) 10 μM CTproSP-C mixed with 50 μM Aβ$_{1-40}$ in ammonium bicarbonate buffer, pH 7-8. In FIG. 9C, the ion observed at m/z 3484 in the mixed sample in FIG. 9B was selected for MS/MS, the collision voltage used was 80 V. FIG. 9D is an enlargement of the m/z range between 1000 and 1600 from FIG. 9C, with peaks corresponding to Aβ$_{1-40}$ released from the CTproSP-C/Aβ complex labelled.

The collision voltage was increased from 10 to 80 V, which apparently was enough to disrupt part of the complex. This yielded a number of daughter ions, mainly corresponding to monomers of CTproSP-C and Aβ$_{1-40}$, but also to CTproSP-C trimers (FIGS. 9C and 9D). Interestingly, among the daughter ions hexamers of CTproSP-C were found, indicating that a at least a portion of the selected ions in fact corresponds to [6CTproSP-C+2Aβ]$^{34+}$ or larger heteromers. Also present in the spectrum after collision was a heteromer consisting of dimeric CTproSP-C and monomeric Aβ$_{1-40}$ with 10 (m/z 4087) and 9 (m/z 4541) charges, which was not found in MS mode (FIGS. 9C and 9D).

Thus, using ESI mass spectrometry the main complex found was a CTproSP-C trimer interacting with monomeric Aβ (FIG. 8). CID experiments confirmed the Aβ/CTproSP-C nature of the complex (FIG. 9). The stoichiometries of the CTproSP-C/Aβ complexes apparently differ between SEC and ESI-MS data. ESI-MS might be more efficient than SEC in breaking up Aβ micelles or similar aggregates, without disrupting direct CTproSP-C/Aβ interactions. Combining the SEC and ESI-MS data suggests that a CTproSP-C trimer can bind to one Aβ molecule present in an approximately dodecameric assembly.

Example 11

Chaperone Assays

To assess the ability of CTproSP-C to act as a classical chaperone, i.e. to prevent aggregation of destabilised proteins, assays employing either alcohol dehydrogenase (ADH) or insulin were used.

Heat-induced aggregation of ADH from baker's yeast with and without CTproSP-C present was followed at 50° C. for 15 min by measuring the light scattering (apparent absorption at 360 nm) in a Cary 3 spectrophotometer (Varian Techtron, Mulgrave, Australia). All experiments were carried out with ADH and CTproSP-C concentrations of 6.25 μM each, and the samples were prepared in 20 mM sodium phosphate buffer, pH 7.4, 150 mM sodium chloride.

Figure 10:
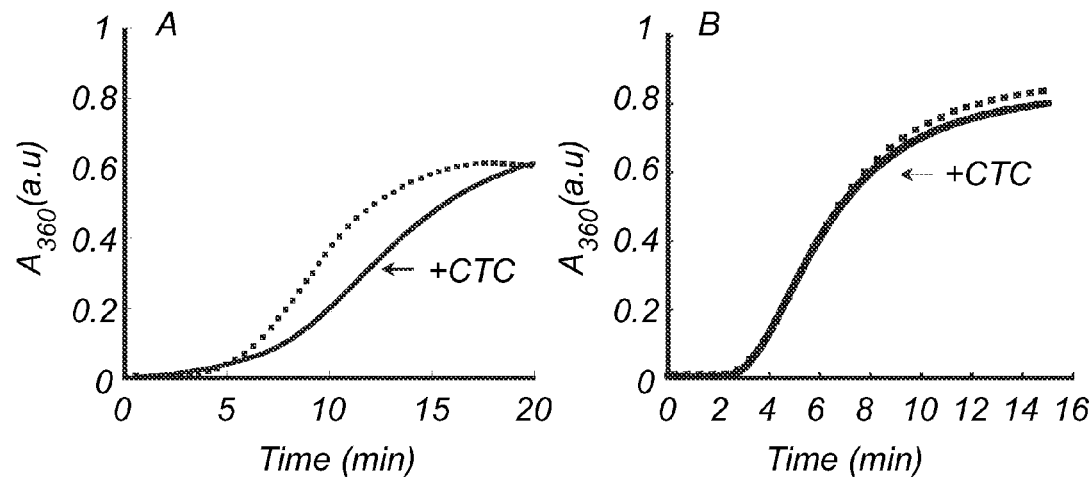
FIG. 10 panels A and B show heat induced aggregation of ADH and reduction-induced aggregation of insulin in the absence and presence of equimolar amounts of CTproSP-C.

FIG. 10A shows heat induced aggregation of ADH in the absence (dotted line) and presence (solid line) of equimolar amounts of CTproSP-C (CTC). At 50° C. ADH started to aggregate within 5 min. Addition of CTproSP-C in equimolar amounts resulted in a minor prolongation of the lag phase before ADH aggregation. This effect is small compared to the effects of a chaperone like e.g. the sHsp α-crystallin which results in complete prevention of ADH aggregation (J I Clark & Q L Huang, Proc Natl Acad Sci USA 93: 15185-15189, 1996).

Reduction-induced aggregation of the β-chain of insulin with and without CTproSP-C was likewise monitored by measuring the apparent absorption at 360 nm. A solution containing 40 μM insulin (Sigma, Sweden) in 50 mM sodium phosphate buffer, pH 7.0, 100 mM sodium chloride, with or without CTproSP-C, at a molar ratio of 1:1, was preincubated for 5 min at 41° C. Dithiothreitol (DTT) was then added to a final concentration of 20 μM, and the change in absorption at 360 nm was monitored for 15 min at 41° C.

FIG. 10B shows reduction-induced aggregation of insulin in the absence (dotted line) and presence (solid line) of equimolar amounts of CTproSP-C (CTC). Reduction of insulin at 41° C. results in aggregation starting after about 3 min. Addition of CTproSP-C at a molar ratio of 1:1 did not affect insulin aggregation at all.

It appears from these results that CTproSP-C is unable to prevent aggregation of ADH and insulin. This indicates that CTproSP-C does not possess the typical properties of traditional chaperones, such as Hsp70 or sHsps.

Example 12

Substrate Binding Specificity of CTproSP-C and its Brichos Domain

A truncated human CTproSP-C was produced as described in Example 1. This protein starts at position 86 in proSP-C, as compared to position 94 for the original Brichos domain construct, resulting in an extended version of the Brichos domain of human CTproSP-C. The sequence of the extended CTproSP-C$_{Brichos}$ protein is SEQ ID NO: 21.

Figure 11:
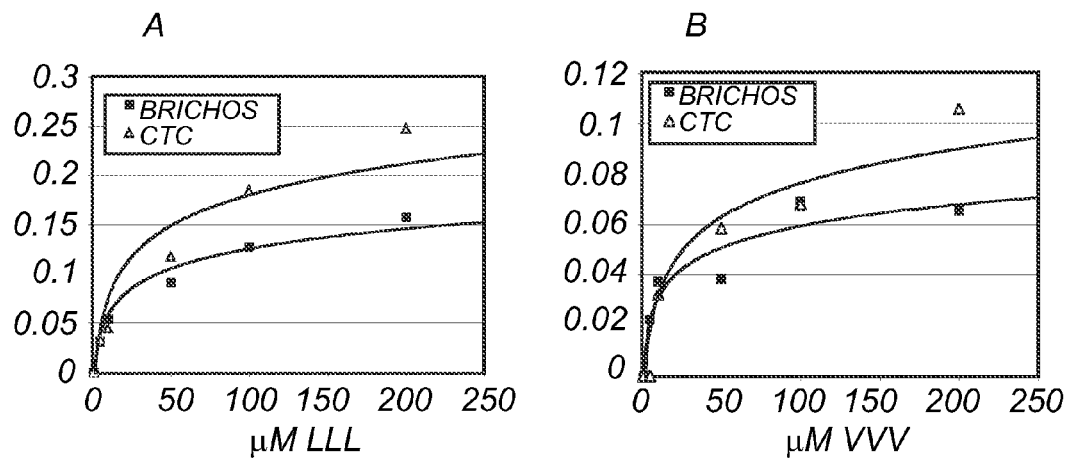
FIG. 11 panels A and B show relative binding of target peptides to CTproSP-C or a truncated CTproSP-C as a function of target peptide concentration.

The substrate binding specificities of the extended CTproSP-C$_{Brichos}$ and CTproSP-C were investigated by ESI-MS in presence of various concentrations of the tripeptides VVV and LLL. Relative concentrations of protein-tripeptide heteromers [PL] and protein (i.e. extended CTproSP-C$_{Brichos}$ or CTproSP-C) [P] were determined from deconvolution spectra. The ratio of [PL]/[P] was plotted as a function of tripeptide concentration to obtain binding curves for both proteins and both ligands. As shown in FIG. 11, the extended CTproSP-C$_{Brichos}$ ("BRICHOS") and CTproSP-C ("CTC") were found to bind the two tripeptides LLL (FIG. 11A) and VVV (FIG. 11 B) in a similar manner. Thus, an extended Brichos domain has the same substrate binding profile as full-length CTproSP-C.

Example 13

Circular Dichroism (CD) Spectroscopy Study with Aβ Peptides and CTC

Aβ forms β-sheet structures that lead to its aggregation and finally formation of fibrils. Our aim is to determine if CTproSP-C would stabilize the Aβ peptide in random coil state, thus preventing the Aβ peptide from forming β-sheets and fibrils. CTproSP-C is a protein which has been found to interact with Aβ peptide. We used Aβ(1-40) as well as Aβ(1-42) to study their interactions with CTproSP-C, using CD spectroscopy.

The Aβ peptides were pretreated with TFA and HFIP followed by solubilization in 20 mM NaOH at a concentration of 200 μM by vortexing and sonication. The peptide solutions were then diluted with 10 mM phosphate buffer, pH 7, to a final peptide concentration of 20 μM. The CTproSP-C was used at a concentration of 20 μM. CD spectra in the far-UV region (190-260 nm) were recorded at 22° C. with a Jasco J-810-150S spectropolarimeter (Jasco, Tokyo, Japan) using a bandwidth of 1 nm and a response time of 2 s, and 10 data points/nm were collected. The CD signal in mdeg as a function of wavelength were plotted.

Aβ(1-40) as well as Aβ(1-42) convert from a mainly random secondary structure at time=0 to a structure dominated by β-sheet already after a few hours. In contrast to the behaviour of Aβ(1-40) or Aβ(1-42) alone, the presence of CTproSP-C at equimolar amounts keeps the Aβ conformation virtually unchanged for at least 5 hours. From CD spectra of mixtures of CTproSP-C with Aβ(1-40) or Aβ(1-42), the contribution from CTproSP-C was subtracted. The resulting spectra show that both Aβ peptides stay in mainly random conformation, thereby avoiding (3-sheet aggregation, over the observation period.

An alternative way to present the same data is to plot the evolution of the amplitude of the CD signal at 217 nm (a measure of (3-sheet content) over time for Aβ(1-40) as well as Aβ(1-42) with and without CTproSP-C "CTC", as shown in FIG. 12. This shows show that while for Aβ(1-40) (FIG. 12A) or Aβ(1-42) (FIG. 12B) the $CD_{217nm}$ signal amplitude increases over time (squares), the presence (1:1) of CTproSP-C (circles) largely abolishes this increase.

These results show that human CTproSP-C has similar structural effects on Aβ(1-40) and $Aβ_{1-42}$).

Example 14

Cell Culture Experiments

Aβ polymerization generates assemblies that are toxic to cells in culture. MTT (3-(4,5-dimethylthiazol-2-yl)-2,5-diphenyltetrazolium bromide) is employed to monitor oxidative capacity of PC12 cells after treatment with $Aβ_{1-42}$ polymerized in the absence or presence of CTproSP-C or $CTproSP-C_{Brichos}$.

PC12 cells are cultured in 5% carbon dioxide in DMEM medium supplemented with 10% fetal calf serum and penicillin/streptomycin (National Veterinary Institute, Sweden). The cells are plated at an appropriate density in 96-well Cell+ plates (Sarstedt, Sweden). The following day, the media is exchanged to DMEM without phenol red (45 µl/well) supplemented with 10% fetal calf serum and penicillin/streptomycin. Typically, $Aβ_{1-42}$ at 10 µM is added (5 µl/well) resulting in a final concentration of 1 µM either directly (4 h treatment experiment) or after 4 h pre-incubation at 37° C. (18 h treatment experiment), alone or with CTproSP-C or CTproSP-$C_{Brichos}$ at equimolar or five times molar excess concentration. PBS with the same amount of solvent used for the Aβ preparations is used as control treatment. The cells are incubated for 4 or 18 h with treatment and thereafter MTT dissolved at 0.6 mg/ml in DMEM without phenol red is added (50 µl/well), resulting in a final concentration of 0.3 mg/ml MTT, and incubated with the cells for 2 h at 37° C. The purple formazan crystals are dissolved using a solubilisation buffer containing 50% dimethylformamide and 20% SDS in water added directly to the cell culture media (100 µl/well). Absorbance at 575 nm is recorded and control treatment set to 100% viable cells.

Example 15

Experiments in Transgenic Mice

Mice expressing the human Aβ precursor (APP) with one or several mutations linked to Alzheimer's in man are typically used for evaluation of treatment strategies. To mice expressing APP with the Swedish mutation (APP K670N/M671L) only, or the Swedish mutation plus the Arctic mutation (APP E693G) (Lord A et al., Neurobiol Aging 27: 67-77, 2006), CTproSP-C or CTproSP-$C_{Brichos}$ is administered intravenously, intraperitoneally, intranasally, or intracranially in doses of 3-15 mg/kg, once to three times a week, for 10-30 weeks. The effects of the treatments are evaluated by histological examination of plaque deposition in the CNS compared to sham- or non-treated controls, although other measures such as amounts of soluble and non-soluble Aβ and behavioral parameters are also used.

Example 16

Administration to Man

CTproSP-C or CTproSP-$C_{Brichos}$ is administered intravenously, intraperitoneally, intranasally, or intracranially in doses of 3-15 mg/kg, once to three times a week, for 10-30 weeks to healthy individuals and individuals suffering from Alzheimer's disease. The effects of the treatments are evaluated by histological examination of plaque deposition in the CNS compared to sham- or non-treated controls. Other measures, such as amounts of soluble and non-soluble Aβ and behavioral parameters, are also used.

The invention claimed is:

1. A method of therapeutically treating or delaying progression of Alzheimer's disease in a subject in need thereof, comprising administering to the subject a therapeutically effective amount of an isolated protein, wherein the isolated protein delays or reduces amyloid fibril formation and aggregation of amyloid β peptide, and wherein the isolated protein is selected from (a) a protein comprising an amino acid sequence having at least 80% identity to the CTpro-SP-C from human (SEQ ID NO: 2) and (b) a protein comprising an amino acid sequence having at least 80% identity to a Brichos domain of CTproSP-C from human (SEQ ID NO: 4);
   wherein the isolated protein has more than or equal to 90 amino acid residues, and less than or equal to 150 amino acid residues; and
   wherein the position corresponding to leucine-188 in human proSP-C (SEQ ID NO: 1) is strictly conserved.

2. The method of claim 1, wherein the isolated protein has more than or equal to 100 amino acid residues.

3. The method of claim 1, wherein the isolated protein comprises an amino acid sequence having at least 80% identity to SEQ ID NO: 2.

4. The method of claim 1, wherein the isolated protein comprises an amino acid sequence having at least 80% identity to SEQ ID NO:4.

5. The method of claim 3, wherein the isolated protein comprises an amino acid sequence having at least 90% identity to SEQ ID NO: 2.

6. The method of claim 4, wherein the isolated protein comprises an amino acid sequence having at least 90% identity to SEQ ID NO:4.

* * * * *

SEQUENCE LISTING

```
<160> NUMBER OF SEQ ID NOS: 38

<210> SEQ ID NO 1
<211> LENGTH: 197
<212> TYPE: PRT
<213> ORGANISM: Homo sapiens

<400> SEQUENCE: 1

Met Asp Val Gly Ser Lys Glu Val Leu Met Glu Ser Pro Pro Asp Tyr
1               5                   10                  15

Ser Ala Ala Pro Arg Gly Arg Phe Gly Ile Pro Cys Cys Pro Val His
            20                  25                  30

Leu Lys Arg Leu Leu Ile Val Val Val Val Val Val Leu Ile Val Val
        35                  40                  45

Val Ile Val Gly Ala Leu Leu Met Gly Leu His Met Ser Gln Lys His
    50                  55                  60

Thr Glu Met Val Leu Glu Met Ser Ile Gly Ala Pro Glu Ala Gln Gln
65                  70                  75                  80
```

```
Arg Leu Ala Leu Ser Glu His Leu Val Thr Ala Thr Phe Ser Ile
                85                  90                  95

Gly Ser Thr Gly Leu Val Val Tyr Asp Tyr Gln Gln Leu Leu Ile Ala
            100                 105                 110

Tyr Lys Pro Ala Pro Gly Thr Cys Cys Tyr Ile Met Lys Ile Ala Pro
        115                 120                 125

Glu Ser Ile Pro Ser Leu Glu Ala Leu Asn Arg Lys Val His Asn Phe
    130                 135                 140

Gln Met Glu Cys Ser Leu Gln Ala Lys Pro Ala Val Pro Thr Ser Lys
145                 150                 155                 160

Leu Gly Gln Ala Glu Gly Arg Asp Ala Gly Ser Ala Pro Ser Gly Gly
                165                 170                 175

Asp Pro Ala Phe Leu Gly Met Ala Val Asn Thr Leu Cys Gly Glu Val
            180                 185                 190

Pro Leu Tyr Tyr Ile
        195

<210> SEQ ID NO 2
<211> LENGTH: 139
<212> TYPE: PRT
<213> ORGANISM: Homo sapiens

<400> SEQUENCE: 2

His Met Ser Gln Lys His Thr Glu Met Val Leu Glu Met Ser Ile Gly
1               5                   10                  15

Ala Pro Glu Ala Gln Gln Arg Leu Ala Leu Ser Glu His Leu Val Thr
            20                  25                  30

Thr Ala Thr Phe Ser Ile Gly Ser Thr Gly Leu Val Val Tyr Asp Tyr
        35                  40                  45

Gln Gln Leu Leu Ile Ala Tyr Lys Pro Ala Pro Gly Thr Cys Cys Tyr
    50                  55                  60

Ile Met Lys Ile Ala Pro Glu Ser Ile Pro Ser Leu Glu Ala Leu Asn
65                  70                  75                  80

Arg Lys Val His Asn Phe Gln Met Glu Cys Ser Leu Gln Ala Lys Pro
                85                  90                  95

Ala Val Pro Thr Ser Lys Leu Gly Gln Ala Glu Gly Arg Asp Ala Gly
            100                 105                 110

Ser Ala Pro Ser Gly Gly Asp Pro Ala Phe Leu Gly Met Ala Val Asn
        115                 120                 125

Thr Leu Cys Gly Glu Val Pro Leu Tyr Tyr Ile
    130                 135

<210> SEQ ID NO 3
<211> LENGTH: 35
<212> TYPE: PRT
<213> ORGANISM: Homo sapiens

<400> SEQUENCE: 3

Phe Gly Ile Pro Cys Cys Pro Val His Leu Lys Arg Leu Leu Ile Val
1               5                   10                  15

Val Val Val Val Leu Ile Val Val Ile Val Gly Ala Leu Leu
            20                  25                  30

Met Gly Leu
        35

<210> SEQ ID NO 4
<211> LENGTH: 104
```

<212> TYPE: PRT
<213> ORGANISM: Homo sapiens

<400> SEQUENCE: 4

```
Phe Ser Ile Gly Ser Thr Gly Leu Val Val Tyr Asp Tyr Gln Gln Leu
1               5                   10                  15

Leu Ile Ala Tyr Lys Pro Ala Pro Gly Thr Cys Cys Tyr Ile Met Lys
            20                  25                  30

Ile Ala Pro Glu Ser Ile Pro Ser Leu Glu Ala Leu Asn Arg Lys Val
        35                  40                  45

His Asn Phe Gln Met Glu Cys Ser Leu Gln Ala Lys Pro Ala Val Pro
    50                  55                  60

Thr Ser Lys Leu Gly Gln Ala Glu Gly Arg Asp Ala Gly Ser Ala Pro
65                  70                  75                  80

Ser Gly Gly Asp Pro Ala Phe Leu Gly Met Ala Val Asn Thr Leu Cys
                85                  90                  95

Gly Glu Val Pro Leu Tyr Tyr Ile
                100
```

<210> SEQ ID NO 5
<211> LENGTH: 132
<212> TYPE: PRT
<213> ORGANISM: Bos taurus

<400> SEQUENCE: 5

```
His Met Ser Gln Lys His Thr Glu Met Val Leu Glu Met Ser Ile Thr
1               5                   10                  15

Gly Pro Glu Ala Gln Gln Arg Leu Ala Leu Ser Glu Arg Val Gly Thr
            20                  25                  30

Thr Ala Thr Phe Ser Ile Gly Ser Thr Gly Thr Val Val Tyr Asp Tyr
        35                  40                  45

Gln Arg Leu Leu Ile Ala Tyr Lys Pro Ala Pro Gly Thr Cys Cys Tyr
    50                  55                  60

Ile Met Lys Met Ala Pro Gln Asn Ile Pro Ser Leu Glu Ala Leu Thr
65                  70                  75                  80

Arg Lys Leu Gln Asn Phe Gln Ala Lys Pro Gln Val Pro Ser Ser Lys
                85                  90                  95

Leu Gly Gln Glu Gln Gly His Asp Ala Gly Ser Ala Phe Ser Gly Asp
                100                 105                 110

Leu Ala Phe Leu Gly Arg Thr Val Ser Thr Leu Cys Gly Glu Val Pro
            115                 120                 125

Leu Tyr Tyr Thr
    130
```

<210> SEQ ID NO 6
<211> LENGTH: 133
<212> TYPE: PRT
<213> ORGANISM: Macaca mulatta

<400> SEQUENCE: 6

```
His Met Ser Gln Lys His Thr Glu Met Val Leu Glu Met Ser Ile Gly
1               5                   10                  15

Ala Pro Glu Ala Gln Gln His Leu Ala Arg Ser Gly His Leu Val Thr
            20                  25                  30

Thr Ala Thr Phe Ser Phe Gly Ser Thr Gly Leu Val Val Tyr Asp Tyr
        35                  40                  45

Gln Arg Leu Leu Ile Ala Tyr Lys Pro Ala Pro Gly Thr Trp Cys Tyr
```

```
                 50                  55                  60

Ile Met Lys Thr Ala Pro Glu Ser Ile Pro Ser Leu Glu Ala Leu Thr
 65                  70                  75                  80

Arg Lys Val Gln Asn Phe Gln Ala Lys Pro Ala Val Pro Thr Ser Lys
                 85                  90                  95

Leu Asp Gln Val Glu Gly Arg Asp Ala Gly Ser Ala Pro Ser Arg Gly
                100                 105                 110

Asp Leu Ala Phe Leu Gly Met Ala Val Ser Thr Leu Cys Gly Glu Val
            115                 120                 125

Pro Leu Tyr Tyr Ile
        130

<210> SEQ ID NO 7
<211> LENGTH: 135
<212> TYPE: PRT
<213> ORGANISM: Mus musculus

<400> SEQUENCE: 7

His Met Ser Gln Lys His Thr Glu Met Val Leu Glu Met Ser Ile Gly
 1               5                  10                  15

Ala Pro Glu Thr Gln Lys Arg Leu Ala Pro Ser Glu Arg Ala Asp Thr
                 20                  25                  30

Ile Ala Thr Phe Ser Ile Gly Ser Thr Gly Ile Val Val Tyr Asp Tyr
             35                  40                  45

Gln Arg Leu Leu Thr Ala Tyr Lys Pro Ala Pro Gly Thr Tyr Cys Tyr
         50                  55                  60

Ile Met Lys Met Ala Pro Glu Ser Ile Pro Ser Leu Glu Ala Phe Ala
 65                  70                  75                  80

Arg Lys Leu Gln Asn Phe Arg Ala Lys Pro Ser Thr Pro Thr Ser Lys
                 85                  90                  95

Leu Gly Gln Glu Glu Gly His Asp Thr Gly Ser Glu Ser Asp Ser Ser
                100                 105                 110

Gly Arg Asp Leu Ala Phe Leu Gly Leu Ala Val Ser Thr Leu Cys Gly
            115                 120                 125

Glu Leu Pro Leu Tyr Tyr Ile
        130                 135

<210> SEQ ID NO 8
<211> LENGTH: 132
<212> TYPE: PRT
<213> ORGANISM: Mustela vison

<400> SEQUENCE: 8

His Met Ser Gln Lys His Thr Glu Met Val Leu Glu Met Ser Leu Gly
 1               5                  10                  15

Gly Pro Glu Ala Gln Gln Arg Leu Ala Leu Gln Glu Arg Ala Gly Thr
                 20                  25                  30

Thr Ala Thr Phe Ser Ile Gly Ser Thr Gly Ile Val Val Tyr Asp Tyr
             35                  40                  45

Gln Arg Leu Leu Ile Ala Tyr Lys Pro Ala Pro Gly Thr Cys Cys Tyr
         50                  55                  60

Ile Met Lys Met Ala Pro Glu Asn Ile Pro Ser Leu Glu Ala Leu Thr
 65                  70                  75                  80

Arg Lys Phe Gln Asn Phe Gln Val Lys Pro Ala Val Ser Thr Ser Lys
                 85                  90                  95

Leu Gly Gln Glu Glu Gly His Asn Ala Gly Ser Ala Ser Pro Gly Asp
```

```
                100                 105                 110
Leu Asp Phe Leu Gly Thr Thr Val Ser Thr Leu Cys Gly Glu Val Pro
        115                 120                 125
Leu Tyr Tyr Ile
    130

<210> SEQ ID NO 9
<211> LENGTH: 130
<212> TYPE: PRT
<213> ORGANISM: Oryctolagus cuniculus

<400> SEQUENCE: 9

His Met Ser Gln Lys His Thr Glu Met Val Leu Glu Met Ser Ile Gly
1               5                   10                  15

Ala Pro Glu Val Gln Gln Arg Leu Ala Leu Ser Glu Trp Ala Gly Thr
            20                  25                  30

Thr Ala Thr Phe Pro Ile Gly Ser Thr Gly Ile Val Thr Cys Asp Tyr
        35                  40                  45

Gln Arg Leu Leu Ile Ala Tyr Lys Pro Ala Pro Gly Thr Cys Cys Tyr
    50                  55                  60

Leu Met Lys Met Ala Pro Asp Ser Ile Pro Ser Leu Glu Ala Leu Ala
65                  70                  75                  80

Arg Lys Phe Gln Ala Asn Pro Ala Glu Pro Thr Gln Arg Gly Gln
                85                  90                  95

Asp Lys Gly Pro Ala Ala Gly Pro Ala Ser Ser Gly Gly Glu Leu Ala
            100                 105                 110

Phe Leu Gly Ala Ala Val Ser Thr Leu Cys Gly Glu Val Pro Leu Ile
        115                 120                 125

Tyr Ile
    130

<210> SEQ ID NO 10
<211> LENGTH: 136
<212> TYPE: PRT
<213> ORGANISM: Rattus norvegicus

<400> SEQUENCE: 10

His Met Ser Gln Lys His Thr Glu Met Val Leu Glu Met Ser Ile Gly
1               5                   10                  15

Gly Ala Pro Glu Thr Gln Lys Arg Leu Ala Leu Ser Glu His Thr Asp
            20                  25                  30

Thr Ile Ala Thr Phe Ser Ile Gly Ser Thr Gly Ile Val Leu Tyr Asp
        35                  40                  45

Tyr Gln Arg Leu Leu Thr Ala Tyr Lys Pro Ala Pro Gly Thr Tyr Cys
    50                  55                  60

Tyr Ile Met Lys Met Ala Pro Glu Ser Ile Pro Ser Leu Glu Ala Leu
65                  70                  75                  80

Ala Arg Lys Phe Lys Asn Phe Gln Ala Lys Ser Ser Thr Pro Thr Ser
                85                  90                  95

Lys Leu Gly Gln Glu Glu Gly His Ser Ala Gly Ser Asp Ser Asp Ser
            100                 105                 110

Ser Gly Arg Asp Leu Ala Phe Leu Gly Leu Ala Val Ser Thr Leu Cys
        115                 120                 125

Gly Glu Leu Pro Leu Tyr Tyr Ile
    130                 135
```

-continued

```
<210> SEQ ID NO 11
<211> LENGTH: 142
<212> TYPE: PRT
<213> ORGANISM: Artificial Sequence
<220> FEATURE:
<223> OTHER INFORMATION: Strictly conserved sequence in mammals
<220> FEATURE:
<221> NAME/KEY: MISC_FEATURE
<222> LOCATION: (15)..(18)
<223> OTHER INFORMATION: Not strictly conserved amino acid residues
<220> FEATURE:
<221> NAME/KEY: MISC_FEATURE
<222> LOCATION: (21)..(21)
<223> OTHER INFORMATION: Not strictly conserved amino acid residue
<220> FEATURE:
<221> NAME/KEY: MISC_FEATURE
<222> LOCATION: (23)..(24)
<223> OTHER INFORMATION: Not strictly conserved amino acid residues
<220> FEATURE:
<221> NAME/KEY: MISC_FEATURE
<222> LOCATION: (27)..(32)
<223> OTHER INFORMATION: Not strictly conserved amino acid residues
<220> FEATURE:
<221> NAME/KEY: MISC_FEATURE
<222> LOCATION: (34)..(34)
<223> OTHER INFORMATION: Not strictly conserved amino acid residue
<220> FEATURE:
<221> NAME/KEY: MISC_FEATURE
<222> LOCATION: (38)..(39)
<223> OTHER INFORMATION: Not strictly conserved amino acid residues
<220> FEATURE:
<221> NAME/KEY: MISC_FEATURE
<222> LOCATION: (44)..(44)
<223> OTHER INFORMATION: Not strictly conserved amino acid residue
<220> FEATURE:
<221> NAME/KEY: MISC_FEATURE
<222> LOCATION: (46)..(47)
<223> OTHER INFORMATION: Not strictly conserved amino acid residues
<220> FEATURE:
<221> NAME/KEY: MISC_FEATURE
<222> LOCATION: (51)..(51)
<223> OTHER INFORMATION: Not strictly conserved amino acid residue
<220> FEATURE:
<221> NAME/KEY: MISC_FEATURE
<222> LOCATION: (54)..(54)
<223> OTHER INFORMATION: Not strictly conserved amino acid residue
<220> FEATURE:
<221> NAME/KEY: MISC_FEATURE
<222> LOCATION: (63)..(63)
<223> OTHER INFORMATION: Not strictly conserved amino acid residue
<220> FEATURE:
<221> NAME/KEY: MISC_FEATURE
<222> LOCATION: (66)..(66)
<223> OTHER INFORMATION: Not strictly conserved amino acid residue
<220> FEATURE:
<221> NAME/KEY: MISC_FEATURE
<222> LOCATION: (69)..(69)
<223> OTHER INFORMATION: Not strictly conserved amino acid residue
<220> FEATURE:
<221> NAME/KEY: MISC_FEATURE
<222> LOCATION: (72)..(73)
<223> OTHER INFORMATION: Not strictly conserved amino acid residues
<220> FEATURE:
<221> NAME/KEY: MISC_FEATURE
<222> LOCATION: (80)..(81)
<223> OTHER INFORMATION: Not strictly conserved amino acid residues
<220> FEATURE:
<221> NAME/KEY: MISC_FEATURE
<222> LOCATION: (84)..(105)
<223> OTHER INFORMATION: Not strictly conserved amino acid residues
<220> FEATURE:
<221> NAME/KEY: MISC_FEATURE
<222> LOCATION: (107)..(108)
<223> OTHER INFORMATION: Not strictly conserved amino acid residues
<220> FEATURE:
<221> NAME/KEY: MISC_FEATURE
<222> LOCATION: (110)..(112)
<223> OTHER INFORMATION: Not strictly conserved amino acid residues
<220> FEATURE:
```

```
<221> NAME/KEY: MISC_FEATURE
<222> LOCATION: (114)..(118)
<223> OTHER INFORMATION: Not strictly conserved amino acid residues
<220> FEATURE:
<221> NAME/KEY: MISC_FEATURE
<222> LOCATION: (120)..(124)
<223> OTHER INFORMATION: Not strictly conserved amino acid residues
<220> FEATURE:
<221> NAME/KEY: MISC_FEATURE
<222> LOCATION: (128)..(129)
<223> OTHER INFORMATION: Not strictly conserved amino acid residues
<220> FEATURE:
<221> NAME/KEY: MISC_FEATURE
<222> LOCATION: (131)..(131)
<223> OTHER INFORMATION: Not strictly conserved amino acid residue
<220> FEATURE:
<221> NAME/KEY: MISC_FEATURE
<222> LOCATION: (137)..(137)
<223> OTHER INFORMATION: Not strictly conserved amino acid residue
<220> FEATURE:
<221> NAME/KEY: MISC_FEATURE
<222> LOCATION: (140)..(140)
<223> OTHER INFORMATION: Not strictly conserved amino acid residue
<220> FEATURE:
<221> NAME/KEY: MISC_FEATURE
<222> LOCATION: (142)..(142)
<223> OTHER INFORMATION: Not strictly conserved amino acid residue

<400> SEQUENCE: 11

His Met Ser Gln Lys His Thr Glu Met Val Leu Glu Met Ser Xaa Xaa
1               5                   10                  15

Xaa Xaa Pro Glu Xaa Gln Xaa Xaa Leu Ala Xaa Xaa Xaa Xaa Xaa Xaa
                20                  25                  30

Thr Xaa Ala Thr Phe Xaa Xaa Gly Ser Thr Gly Xaa Val Xaa Xaa Asp
        35                  40                  45

Tyr Gln Xaa Leu Leu Xaa Ala Tyr Lys Pro Ala Pro Gly Thr Xaa Cys
50                  55                  60

Tyr Xaa Met Lys Xaa Ala Pro Xaa Xaa Ile Pro Ser Leu Glu Ala Xaa
65                  70                  75                  80

Xaa Arg Lys Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Gln Xaa Xaa Gly Xaa Xaa Xaa Xaa
                100                 105                 110

Gly Xaa Xaa Xaa Xaa Xaa Ser Xaa Xaa Xaa Xaa Xaa Phe Leu Gly Xaa
        115                 120                 125

Xaa Val Xaa Thr Leu Cys Gly Glu Xaa Pro Leu Xaa Tyr Xaa
        130                 135                 140

<210> SEQ ID NO 12
<211> LENGTH: 97
<212> TYPE: PRT
<213> ORGANISM: Bos taurus

<400> SEQUENCE: 12

Phe Ser Ile Gly Ser Thr Gly Thr Val Val Tyr Asp Tyr Gln Arg Leu
1               5                   10                  15

Leu Ile Ala Tyr Lys Pro Ala Pro Gly Thr Cys Cys Tyr Ile Met Lys
                20                  25                  30

Met Ala Pro Gln Asn Ile Pro Ser Leu Glu Ala Leu Thr Arg Lys Leu
        35                  40                  45

Gln Asn Phe Gln Ala Lys Pro Gln Val Pro Ser Ser Lys Leu Gly Gln
50                  55                  60

Glu Gln Gly His Asp Ala Gly Ser Ala Phe Ser Gly Asp Leu Ala Phe
65                  70                  75                  80
```

```
Leu Gly Arg Thr Val Ser Thr Leu Cys Gly Glu Val Pro Leu Tyr Tyr
                85                  90                  95
Thr

<210> SEQ ID NO 13
<211> LENGTH: 98
<212> TYPE: PRT
<213> ORGANISM: Macaca mulatta

<400> SEQUENCE: 13

Phe Ser Phe Gly Ser Thr Gly Leu Val Val Tyr Asp Tyr Gln Arg Leu
1               5                   10                  15
Leu Ile Ala Tyr Lys Pro Ala Pro Gly Thr Trp Cys Tyr Ile Met Lys
            20                  25                  30
Thr Ala Pro Glu Ser Ile Pro Ser Leu Glu Ala Leu Thr Arg Lys Val
        35                  40                  45
Gln Asn Phe Gln Ala Lys Pro Ala Val Pro Thr Ser Lys Leu Asp Gln
    50                  55                  60
Val Glu Gly Arg Asp Ala Gly Ser Ala Pro Ser Arg Gly Asp Leu Ala
65                  70                  75                  80
Phe Leu Gly Met Ala Val Ser Thr Leu Cys Gly Glu Val Pro Leu Tyr
                85                  90                  95
Tyr Ile

<210> SEQ ID NO 14
<211> LENGTH: 100
<212> TYPE: PRT
<213> ORGANISM: Mus musculus

<400> SEQUENCE: 14

Phe Ser Ile Gly Ser Thr Gly Ile Val Val Tyr Asp Tyr Gln Arg Leu
1               5                   10                  15
Leu Thr Ala Tyr Lys Pro Ala Pro Gly Thr Tyr Cys Tyr Ile Met Lys
            20                  25                  30
Met Ala Pro Glu Ser Ile Pro Ser Leu Glu Ala Phe Ala Arg Lys Leu
        35                  40                  45
Gln Asn Phe Arg Ala Lys Pro Ser Thr Pro Thr Ser Lys Leu Gly Gln
    50                  55                  60
Glu Glu Gly His Asp Thr Gly Ser Glu Ser Asp Ser Ser Gly Arg Asp
65                  70                  75                  80
Leu Ala Phe Leu Gly Leu Ala Val Ser Thr Leu Cys Gly Glu Leu Pro
                85                  90                  95
Leu Tyr Tyr Ile
            100

<210> SEQ ID NO 15
<211> LENGTH: 97
<212> TYPE: PRT
<213> ORGANISM: Mustela vison

<400> SEQUENCE: 15

Phe Ser Ile Gly Ser Thr Gly Ile Val Val Tyr Asp Tyr Gln Arg Leu
1               5                   10                  15
Leu Ile Ala Tyr Lys Pro Ala Pro Gly Thr Cys Cys Tyr Ile Met Lys
            20                  25                  30
Met Ala Pro Glu Asn Ile Pro Ser Leu Glu Ala Leu Thr Arg Lys Phe
        35                  40                  45
```

```
Gln Asn Phe Gln Val Lys Pro Ala Val Ser Thr Ser Lys Leu Gly Gln
         50                  55                  60

Glu Glu Gly His Asn Ala Gly Ser Ala Ser Pro Gly Asp Leu Asp Phe
 65                  70                  75                  80

Leu Gly Thr Thr Val Ser Thr Leu Cys Gly Glu Val Pro Leu Tyr Tyr
                 85                  90                  95

Ile

<210> SEQ ID NO 16
<211> LENGTH: 95
<212> TYPE: PRT
<213> ORGANISM: Oryctolagus cuniculus

<400> SEQUENCE: 16

Phe Pro Ile Gly Ser Thr Gly Ile Val Thr Cys Asp Tyr Gln Arg Leu
  1               5                  10                  15

Leu Ile Ala Tyr Lys Pro Ala Pro Gly Thr Cys Cys Tyr Leu Met Lys
                 20                  25                  30

Met Ala Pro Asp Ser Ile Pro Ser Leu Glu Ala Leu Ala Arg Lys Phe
             35                  40                  45

Gln Ala Asn Pro Ala Glu Pro Pro Thr Gln Arg Gly Gln Asp Lys Gly
         50                  55                  60

Pro Ala Ala Gly Pro Ala Ser Ser Gly Gly Glu Leu Ala Phe Leu Gly
 65                  70                  75                  80

Ala Ala Val Ser Thr Leu Cys Gly Glu Val Pro Leu Ile Tyr Ile
                 85                  90                  95

<210> SEQ ID NO 17
<211> LENGTH: 100
<212> TYPE: PRT
<213> ORGANISM: Rattus norvegicus

<400> SEQUENCE: 17

Phe Ser Ile Gly Ser Thr Gly Ile Val Leu Tyr Asp Tyr Gln Arg Leu
  1               5                  10                  15

Leu Thr Ala Tyr Lys Pro Ala Pro Gly Thr Tyr Cys Tyr Ile Met Lys
                 20                  25                  30

Met Ala Pro Glu Ser Ile Pro Ser Leu Glu Ala Leu Ala Arg Lys Phe
             35                  40                  45

Lys Asn Phe Gln Ala Lys Ser Ser Thr Pro Thr Ser Lys Leu Gly Gln
         50                  55                  60

Glu Glu Gly His Ser Ala Gly Ser Asp Ser Asp Ser Ser Gly Arg Asp
 65                  70                  75                  80

Leu Ala Phe Leu Gly Leu Ala Val Ser Thr Leu Cys Gly Glu Leu Pro
                 85                  90                  95

Leu Tyr Tyr Ile
            100

<210> SEQ ID NO 18
<211> LENGTH: 106
<212> TYPE: PRT
<213> ORGANISM: Artificial Sequence
<220> FEATURE:
<223> OTHER INFORMATION: Strictly conserved sequence in mammals
<220> FEATURE:
<221> NAME/KEY: MISC_FEATURE
<222> LOCATION: (2)..(3)
<223> OTHER INFORMATION: Not strictly conserved amino acid residues
<220> FEATURE:
```

```
<221> NAME/KEY: MISC_FEATURE
<222> LOCATION: (8)..(8)
<223> OTHER INFORMATION: Not strictly conserved amino acid residue
<220> FEATURE:
<221> NAME/KEY: MISC_FEATURE
<222> LOCATION: (10)..(11)
<223> OTHER INFORMATION: Not strictly conserved amino acid residues
<220> FEATURE:
<221> NAME/KEY: MISC_FEATURE
<222> LOCATION: (15)..(15)
<223> OTHER INFORMATION: Not strictly conserved amino acid residue
<220> FEATURE:
<221> NAME/KEY: MISC_FEATURE
<222> LOCATION: (18)..(18)
<223> OTHER INFORMATION: Not strictly conserved amino acid residue
<220> FEATURE:
<221> NAME/KEY: MISC_FEATURE
<222> LOCATION: (27)..(27)
<223> OTHER INFORMATION: Not strictly conserved amino acid residue
<220> FEATURE:
<221> NAME/KEY: MISC_FEATURE
<222> LOCATION: (30)..(30)
<223> OTHER INFORMATION: Not strictly conserved amino acid residue
<220> FEATURE:
<221> NAME/KEY: MISC_FEATURE
<222> LOCATION: (33)..(33)
<223> OTHER INFORMATION: Not strictly conserved amino acid residue
<220> FEATURE:
<221> NAME/KEY: MISC_FEATURE
<222> LOCATION: (36)..(37)
<223> OTHER INFORMATION: Not strictly conserved amino acid residues
<220> FEATURE:
<221> NAME/KEY: MISC_FEATURE
<222> LOCATION: (44)..(45)
<223> OTHER INFORMATION: Not strictly conserved amino acid residues
<220> FEATURE:
<221> NAME/KEY: MISC_FEATURE
<222> LOCATION: (48)..(69)
<223> OTHER INFORMATION: Not strictly conserved amino acid residues
<220> FEATURE:
<221> NAME/KEY: MISC_FEATURE
<222> LOCATION: (71)..(72)
<223> OTHER INFORMATION: Not strictly conserved amino acid residues
<220> FEATURE:
<221> NAME/KEY: MISC_FEATURE
<222> LOCATION: (74)..(76)
<223> OTHER INFORMATION: Not strictly conserved amino acid residues
<220> FEATURE:
<221> NAME/KEY: MISC_FEATURE
<222> LOCATION: (78)..(82)
<223> OTHER INFORMATION: Not strictly conserved amino acid residues
<220> FEATURE:
<221> NAME/KEY: MISC_FEATURE
<222> LOCATION: (84)..(88)
<223> OTHER INFORMATION: Not strictly conserved amino acid residues
<220> FEATURE:
<221> NAME/KEY: MISC_FEATURE
<222> LOCATION: (92)..(93)
<223> OTHER INFORMATION: Not strictly conserved amino acid residues
<220> FEATURE:
<221> NAME/KEY: MISC_FEATURE
<222> LOCATION: (95)..(95)
<223> OTHER INFORMATION: Not strictly conserved amino acid residue
<220> FEATURE:
<221> NAME/KEY: MISC_FEATURE
<222> LOCATION: (101)..(101)
<223> OTHER INFORMATION: Not strictly conserved amino acid residue
<220> FEATURE:
<221> NAME/KEY: MISC_FEATURE
<222> LOCATION: (104)..(104)
<223> OTHER INFORMATION: Not strictly conserved amino acid residue
<220> FEATURE:
<221> NAME/KEY: MISC_FEATURE
<222> LOCATION: (106)..(106)
<223> OTHER INFORMATION: Not strictly conserved amino acid residue

<400> SEQUENCE: 18

Phe Xaa Xaa Gly Ser Thr Gly Xaa Val Xaa Xaa Asp Tyr Gln Xaa Leu
```

```
                1               5                  10                  15
            Leu Xaa Ala Tyr Lys Pro Ala Pro Gly Thr Xaa Cys Tyr Xaa Met Lys
                        20                  25                  30

Xaa Ala Pro Xaa Xaa Ile Pro Ser Leu Glu Ala Xaa Xaa Arg Lys Xaa
                        35                  40                  45

Xaa Xaa Xaa Xaa Xaa Xaa Xaa Xaa Xaa Xaa Xaa Xaa Xaa Xaa Xaa Xaa
                        50                  55                  60

Xaa Xaa Xaa Xaa Gln Xaa Xaa Gly Xaa Xaa Xaa Gly Xaa Xaa
             65                 70                  75                  80

Xaa Xaa Ser Xaa Xaa Xaa Xaa Phe Leu Gly Xaa Xaa Val Xaa Thr
                        85                  90                  95

Leu Cys Gly Glu Xaa Pro Leu Xaa Tyr Xaa
                        100                 105

<210> SEQ ID NO 19
<211> LENGTH: 40
<212> TYPE: PRT
<213> ORGANISM: Homo sapiens

<400> SEQUENCE: 19

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val
            35                  40

<210> SEQ ID NO 20
<211> LENGTH: 171
<212> TYPE: PRT
<213> ORGANISM: Artificial Sequence
<220> FEATURE:
<223> OTHER INFORMATION: S-tagged human CTproSP-C
<220> FEATURE:
<221> NAME/KEY: MISC_FEATURE
<222> LOCATION: (1)..(32)
<223> OTHER INFORMATION: S-tag

<400> SEQUENCE: 20

Gly Ser Gly Met Lys Glu Thr Ala Ala Ala Lys Phe Glu Arg Gln His
 1               5                  10                  15

Met Asp Ser Pro Asp Leu Gly Thr Asp Asp Asp Lys Ala Met Ala
            20                  25                  30

His Met Ser Gln Lys His Thr Glu Met Val Leu Glu Met Ser Ile Gly
            35                  40                  45

Ala Pro Glu Ala Gln Gln Arg Leu Ala Leu Ser Glu His Leu Val Thr
            50                  55                  60

Thr Ala Thr Phe Ser Ile Gly Ser Thr Gly Leu Val Val Tyr Asp Tyr
 65                 70                  75                  80

Gln Gln Leu Leu Ile Ala Tyr Lys Pro Ala Pro Gly Thr Cys Cys Tyr
            85                  90                  95

Ile Met Lys Ile Ala Pro Glu Ser Ile Pro Ser Leu Glu Ala Leu Thr
            100                 105                 110

Arg Lys Val His Asn Phe Gln Met Glu Cys Ser Leu Gln Ala Lys Pro
            115                 120                 125

Ala Val Pro Thr Ser Lys Leu Gly Gln Ala Glu Gly Arg Asp Ala Gly
            130                 135                 140

Ser Ala Pro Ser Gly Gly Asp Pro Ala Phe Leu Gly Met Ala Val Ser
```

```
                        145                 150                 155                 160
Thr Leu Cys Gly Glu Val Pro Leu Tyr Tyr Ile
                165                 170

<210> SEQ ID NO 21
<211> LENGTH: 112
<212> TYPE: PRT
<213> ORGANISM: Homo sapiens

<400> SEQUENCE: 21

Glu His Leu Val Thr Thr Ala Thr Phe Ser Ile Gly Ser Thr Gly Leu
1               5                   10                  15

Val Val Tyr Asp Tyr Gln Gln Leu Leu Ile Ala Tyr Lys Pro Ala Pro
            20                  25                  30

Gly Thr Cys Cys Tyr Ile Met Lys Ile Ala Pro Glu Ser Ile Pro Ser
        35                  40                  45

Leu Glu Ala Leu Asn Arg Lys Val His Asn Phe Gln Met Glu Cys Ser
    50                  55                  60

Leu Gln Ala Lys Pro Ala Val Pro Thr Ser Lys Leu Gly Gln Ala Glu
65                  70                  75                  80

Gly Arg Asp Ala Gly Ser Ala Pro Ser Gly Asp Pro Ala Phe Leu
                85                  90                  95

Gly Met Ala Val Asn Thr Leu Cys Gly Glu Val Pro Leu Tyr Tyr Ile
            100                 105                 110

<210> SEQ ID NO 22
<211> LENGTH: 4
<212> TYPE: PRT
<213> ORGANISM: Homo sapiens

<400> SEQUENCE: 22

Leu Val Phe Phe
1

<210> SEQ ID NO 23
<211> LENGTH: 9
<212> TYPE: PRT
<213> ORGANISM: Homo sapiens

<400> SEQUENCE: 23

Ile Ile Gly Leu Met Val Gly Gly Trp
1               5

<210> SEQ ID NO 24
<211> LENGTH: 30
<212> TYPE: DNA
<213> ORGANISM: Artificial Sequence
<220> FEATURE:
<223> OTHER INFORMATION: CTproSP-C(Brichos) forward amplification primer

<400> SEQUENCE: 24
ggtgccatgg ctttctccat cggctccact                                        30

<210> SEQ ID NO 25
<211> LENGTH: 44
<212> TYPE: DNA
<213> ORGANISM: Artificial Sequence
<220> FEATURE:
<223> OTHER INFORMATION: CTproSP-C(Brichos) reverse amplification primer

<400> SEQUENCE: 25
ctctagagga tccggatccc tagatgtagt agagcggcac ctcc                        44
```

```
<210> SEQ ID NO 26
<211> LENGTH: 10
<212> TYPE: PRT
<213> ORGANISM: Homo sapiens

<400> SEQUENCE: 26

Lys Arg Leu Leu Ile Val Val Val Val Val
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Mutant of human SP-C residues 11-20, where
      isoleucines and valines are all replaced with leucines.

<400> SEQUENCE: 27

Lys Arg Leu Leu Leu Leu Leu Leu Leu Leu
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Mutant of human SP-C residues 11-20, where
      leucines, isoleucines, and valines are all replaced with alanines.

<400> SEQUENCE: 28

Lys Arg Ala Ala Ala Ala Ala Ala Ala Ala
1               5                   10

<210> SEQ ID NO 29
<211> LENGTH: 10
<212> TYPE: PRT
<213> ORGANISM: Homo sapiens

<400> SEQUENCE: 29

Arg Leu Leu Ile Val Val Val Val Val Val
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Mutant of human SP-C residues 12-21, where
      isoleucines and valines are all replaced with leucines.

<400> SEQUENCE: 30

Arg Leu Leu Leu Leu Leu Leu Leu Leu Leu
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Mutant of human SP-C residues 12-21, where
      leucines, isoleucines, and valines are all replaced with alanines.

<400> SEQUENCE: 31

Arg Ala Ala Ala Ala Ala Ala Ala Ala Ala
1               5                   10
```

-continued

```
<210> SEQ ID NO 32
<211> LENGTH: 10
<212> TYPE: PRT
<213> ORGANISM: Artificial Sequence
<220> FEATURE:
<223> OTHER INFORMATION: Peptide corresponding to positions 17-26 in
      mutant version of human SP-C sequence with Val substituted for Ile
      at position 23 of the human SP-C

<400> SEQUENCE: 32

Val Val Val Val Val Leu Val Val Val Val
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Poly-leucine 10-mer

<400> SEQUENCE: 33

Leu Leu Leu Leu Leu Leu Leu Leu Leu Leu
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Poly-alanine 10-mer.

<400> SEQUENCE: 34

Ala Ala Ala Ala Ala Ala Ala Ala Ala Ala
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Peptide corresponding to positions 22-31 in
      mutant version of human SP-C sequence with Val substituted for Ile
      at position 23 of the human SP-C

<400> SEQUENCE: 35

Leu Val Val Val Val Ile Val Gly Ala Leu
1               5                   10

<210> SEQ ID NO 36
<211> LENGTH: 18
<212> TYPE: PRT
<213> ORGANISM: Artificial Sequence
<220> FEATURE:
<223> OTHER INFORMATION: Ambivalently helical hydrophobic 18-mer
      peptide.

<400> SEQUENCE: 36

Leu Leu Leu Leu Leu Leu Leu Ile Leu Leu Leu Ile Leu Gly Ala
1               5                   10                  15

Leu Leu

<210> SEQ ID NO 37
<211> LENGTH: 6
<212> TYPE: PRT
<213> ORGANISM: Artificial Sequence
<220> FEATURE:
<223> OTHER INFORMATION: Control, non-target 6-mer peptide.
```

```
<400> SEQUENCE: 37

Ile Pro Cys Cys Pro Val
1               5

<210> SEQ ID NO 38
<211> LENGTH: 35
<212> TYPE: PRT
<213> ORGANISM: Artificial Sequence
<220> FEATURE:
<223> OTHER INFORMATION: Mutant version of human SP-C sequence with
      valine substituted for isoleucine at position 23.

<400> SEQUENCE: 38

Phe Gly Ile Pro Cys Cys Pro Val His Leu Lys Arg Leu Leu Ile Val
1               5                   10                  15

Val Val Val Val Val Leu Val Val Val Val Ile Val Gly Ala Leu Leu
                20                  25                  30

Met Gly Leu
        35
```